United States Patent [19]
Sato et al.

[11] Patent Number: 6,127,318
[45] Date of Patent: Oct. 3, 2000

[54] COMBINATION OF GLYPHOSATE AND A TRIAZOLINONE HERBICIDE

[75] Inventors: Tatsuo Sato, Chofu; Masuo Kuchikata, Ryugasaki, both of Japan; Yoo Yong-Man, Kyungjoo, Rep. of Korea; Kathleen S. Cearnal, Florissant; John L. Killmer, Warson Woods, both of Mo.

[73] Assignee: Monsanto Company, St. Louis, Mo.

[21] Appl. No.: 09/272,867

[22] Filed: Mar. 19, 1999

Related U.S. Application Data

[60] Provisional application No. 60/080,649, Apr. 3, 1998, and provisional application No. 60/105,958, Oct. 28, 1998.

[51] Int. Cl.[7] ................................................. A01N 57/00
[52] U.S. Cl. .............................................................. 504/128
[58] Field of Search ..................................... 504/116, 128

[56] References Cited

U.S. PATENT DOCUMENTS

| | | | |
|---|---|---|---|
| 3,799,758 | 3/1974 | Franz | 71/86 |
| 4,405,531 | 9/1983 | Franz | 260/501 |
| 4,818,275 | 4/1989 | Theodoridis | 71/92 |
| 5,125,958 | 6/1992 | Poss | 71/92 |
| 5,217,520 | 6/1993 | Poss | 504/128 |
| 5,858,920 | 1/1999 | Dahmen et al. | 504/103 |
| 5,935,905 | 8/1999 | Mito | 504/128 |

FOREIGN PATENT DOCUMENTS

| | | |
|---|---|---|
| 10-45516 | 2/1998 | Japan . |
| 11-116408 | 4/1999 | Japan . |

OTHER PUBLICATIONS

F.E. Dayan et al., "Selectivity and Mode of Action of Carfentrazone–ethyl, a Novel Phenyl Triazolinone Herbicide," Pest.Sci, 1997, pp. 65–73, vol. 51, Great Britain.

J.E. Franz et al., "Glyphosate: A Unique Global Herbicide," 1997, pp. 153–163, American Chemical Society, ACS Monograph 189, Washington, D.C., U.S.A.

H.J. Lee et al, "Evaluation of Carfentrazone–ethyl Alone and in Combination with Glyphosate or Glufoeinate for Weed Control in Orchards,", Korean J. Weed Sci., 1st ed., vol. 17 (No. 3), p. 256–261, (Mar. 14, 1997).

H.J. Lee et al, "Evaluation of Carfentrazone–ethyl in Combination with Glyphosate and Glufosinate for Weed Control in Orchards", Proceedings of the Sixteenth Asian–Pacific Weed Science Society Conference, Malaysian Plant Protection Society (Kuala Lumpur, Malaysia), vol. 8 (No. 12), p. 306–309, (Sep. 14, 1997).

J.E. Franz et al, "Combinations with Other Herbicides," Glyphosate: A Unique Global Herbicide w, American Chemical Soceity (Washington, D.C.), p. 211–214, (Mar. 14, 1997).

*Primary Examiner*—S. Mark Clardy
*Assistant Examiner*—Alton Pryor
*Attorney, Agent, or Firm*—James M. Warner; James C. Forbes

[57] ABSTRACT

A composition comprising N-(phosphonomethyl)glycine or a salt thereof and a triazolinone herbicide is described. The composition can optionally comprise inert ingredients such as a surfactant, an emulsifier, a solvent, or a carrier. Triazolinone herbicides of particular interest in this composition include carfentrazone-ethyl and sulfentrazone.

106 Claims, No Drawings

COMBINATION OF GLYPHOSATE AND A TRIAZOLINONE HERBICIDE

This application claims the benefit of priority of U.S. Provisional application Ser. No. 60/080,649 filed Apr. 3, 1998 and of U.S. Provisional application Ser. No. 60/105,958 filed Oct. 28, 1998.

BACKGROUND OF THE INVENTION

1. Field of the Invention

This invention relates to combinations of herbicides used for postemergent control of a broad spectrum of weeds. It also relates to a method of preparing and methods of using such combinations.

2. Description of Related Art

N-(Phosphonomethyl)glycine, also known by its common name glyphosate, is a widely-used broad spectrum postemergent herbicide used to control the growth and proliferation of undesired plants. In its acid form and its various salt forms, glyphosate is highly effective and commercially important for controlling weeds in agricultural, industrial, and residential markets. Typically it is applied to the foliage of the target plant, whereafter it is absorbed by the foliar tissue and translocated throughout the plant. N-(Phosphonomethyl)glycine noncompetitively blocks an important biochemical pathway which is common to virtually all plants, but which is absent in animals. Because of the nature of the biochemical pathway, visual symptoms that a plant has been treated with N-(phosphonomethyl)glycine may not appear until two weeks or more after treatment.

Various forms of N-(phosphonomethyl)glycine have been found to be commercially useful. It is sold and used in its acid form, or in a salt form. N-(Phosphonomethyl)glycine salts which are frequently used to control weeds include mono(isopropylammonium) N-(phosphonomethyl)glycine, monoammonium N-(phosphonomethyl)glycine, monosodium N-(phosphonomethyl)glycine, and monotrimethylsulfonium N-(phosphonomethyl)glycine. However, the range of N-(phosphonomethyl)glycine salts useful for controlling weeds is very broad (J. E. Franz et al., *Glyphosate: A Unique Global Herbicide*, ACS Monograph 189, American Chemical Society, Washington, D.C., 1997, pp. 27–64, herein incorporated by reference).

Numerous studies have been made on the effect of surfactants on the herbicidal action of N-(phosphonomethyl)glycine. Franz et al., pp. 155–161 (herein incorporated by reference) describe in detail the effects of many different surfactants and different classes of surfactants on N-(phosphonomethyl)glycine activity. N-(Phosphonomethyl)glycine has been formulated in a variety of ways, including a liquid, a water soluble granule, and a wettable powder.

Protoporphyrinogen oxidase inhibitor (PPO) herbicides are known to affect plants by inhibiting protoporphyrinogen oxidase in chloroplasts, thereby damaging photosynthesis and other processes. This damage causes early symptoms of tissue necrosis in plants. Some PPO herbicides such as the triazolinones (see, for example, U.S. Pat. No. 5,217,520, herein incorporated by reference) provide good control of broadleaf weeds but are less efficacious in controlling grasses.

Japanese Patent Application Publication Kokai Hei 10-45516 (herein incorporated by reference) describes a composition comprising N-(phosphonomethyl)glycine and a PPO herbicide known as carfentrazone. Carfentrazone is a high-melting solid carboxylic acid useful for postemergent control primarily of broadleaf weeds (U.S. Pat. No. 5,217,520, herein incorporated by reference).

SUMMARY OF THE INVENTION

It would be advantageous to have a combination of N-(phosphonomethyl)glycine or a salt thereof with a triazolinone herbicide which allows rapid uptake by the target plant, early visual symptoms of plant treatment, and control of a broad spectrum of weed species.

A combination of N-(phosphonomethyl)glycine and a PPO herbicide such as a triazolinone is useful for at least two reasons. First, since N-(phosphonomethyl)glycine is a broad-spectrum herbicide, it can supplement the triazolinone and the combination can control a wider spectrum of weed species than the triazolinone herbicide can control alone. Second, the early symptoms caused by the triazolinone can serve as an early marker indicating whether a given plant has been treated with the combination.

A combination of N-(phosphonomethyl)glycine or a salt thereof with a triazolinone herbicide is now described. In one of the several embodiments of the present invention a combination is provided which comprises (a) N-(phosphonomethyl)glycine or a salt thereof, and (b) a triazolinone herbicide or a triazolinone herbicide salt or a triazolinone herbicide tautomer, particularly with a triazolinone acid ester herbicide and with a triazolinone sulfonamide herbicide. As used herein, the term "salt" is meant to include an internal salt, i.e., a zwitterion. A preferred embodiment of the present invention provides a combination of N-(phosphonomethyl)glycine or a salt thereof with carfentrazone-ethyl. Another embodiment of the present invention provides a combination of N-(phosphonomethyl)glycine or a salt thereof with sulfentrazone.

In still another embodiment, the present invention provides a formulation comprising N-(phosphonomethyl)glycine or a salt thereof, a triazolinone herbicide, and a surfactant. A preferred embodiment of the present invention provides a herbicidal composition comprising a triazolinone acid ester herbicide and N-(phosphonomethyl)glycine, wherein the triazolinone acid ester herbicide is dispersed in a mixture comprising an alkoxylated acetylenic diol surfactant and a polyoxyalkylene alkyl ether surfactant. Another preferred embodiment of the present invention provides a herbicidal composition comprising a triazolinone sulfonamide herbicide and N-(phosphonomethyl)glycine, wherein the triazolinone acid ester herbicide is dispersed in a mixture comprising an alkoxylated acetylenic diol surfactant, a polyoxyalkylene alkyl ether surfactant, an alkoxylated organosilicone surfactant, and a phosphate solvent.

The present invention is also provides a process for the preparation of a herbicidal composition wherein the method comprises preparing a dispersion by dispersing a triazolinone herbicide in a mixture comprising:

(i) an alkoxylated acetylenic diol surfactant, and
(ii) a polyoxyalkylene alkyl ether surfactant, and combining with the dispersion N-(phosphonomethyl)-glycine or a salt thereof, to form a dough. A preferred embodiment of the present invention provides such a process wherein the mixture in which the triazolinone herbicide is dispersed further comprises a solvent and/or an alkoxylated organosilicone surfactant.

In one preferred embodiment, the present invention provides a composition comprising N-(phosphonomethyl)glycine or a salt thereof, and a triazolinone herbicide and wherein the N-(phosphonomethyl)glycine or salt thereof is substantially dissolved in an aqueous phase and the triazolinone herbicide is substantially dissolved in a hydrophobic phase. Preferably, the hydrophobic phase is dispersed in the aqueous phase to form an emulsion. The present invention also provides a method of preparing a composition comprising N-(phosphonomethyl)glycine or a salt thereof, and a triazolinone herbicide, wherein the method comprises providing a hydrophobic solution comprising the triazolinone herbicide; providing an aqueous solution comprising N-(phosphonomethyl)glycine or a salt thereof; and dispersing the hydrophobic solution into the aqueous solution to form an emulsion.

The present invention is also directed toward providing a method of treating plants wherein the method comprises contacting foliage of plants with a biologically effective amount of a composition comprising N-(phosphonomethyl) glycine or a salt thereof, and a triazolinone acid ester herbicide. The present invention also provides a method of treating plants wherein the method comprises contacting foliage of plants with a biologically effective amount of a composition comprising N-(phosphonomethyl)glycine or a salt thereof, and a triazolinone sulfonamide herbicide.

Another embodiment of the present invention presents a combination consisting essentially of N-(phosphonomethyl) glycine or a salt thereof and a triazolinone herbicide.

Further scope of the applicability of the present invention will become apparent from the detailed description provided below. However, it should be understood that the following detailed description and examples, while indicating preferred embodiments of the invention, are given by way of illustration only since various changes and modifications within the spirit and scope of the invention will from this detailed description become apparent to those skilled in the art.

DETAILED DESCRIPTION OF THE PREFERRED EMBODIMENTS

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

a. Definitions

The following definitions are provided in order to aid the reader in understanding the detailed description of the present invention:

"Glyphosate" means N-(phosphonomethyl)glycine (CAS Registry Number 1071-83-6) in its acid form, or a N-(phosphonomethyl)glycine salt or a zwitterion of N-(phosphonomethyl)glycine.

"Carfentrazone" means α,2-dichloro-5-(4-(difluoromethyl)-4,5-dihydro-3-methyl-5-oxo-1H-1,2,4-triazol-1-yl)-4-fluorobenzenepropionic acid, CAS Registry Number 128621-72-7, or salts thereof.

"Carfentrazone-ethyl" means ethyl α,2-dichloro-5-(4-(difluoromethyl)-4,5-dihydro-3-methyl-5-oxo-1H-1,2,4-triazol-1-yl)-4-fluorobenzenepropionate, CAS Registry Number 128639-02-1.

"Sulfentrazone" means N-(2,4-dichloro-5-(4-(difluoromethyl)-4,5-dihydro-3-methyl-5-oxo-1H-1,2,4-triazol-1-yl)phenyl)methanesulfonamide, CAS Registry Number 122836-35-5.

"Lower alkyl" or "loweralkyl" means an alkyl group having from 1 to about 10 carbon atoms.

"Phosphate solvent" means an aromatic or aliphatic ester of phosphate which can be used as a solvent. Examples of phosphate solvents include trixylenyl phosphate and 2-ethylhexyl diphenyl phosphate.

"Acid equivalent" or "a.e." means the equivalent molar or weight amount of the acid form of a compound existing as a salt. For example, a 10% by weight solution of mono (isopropylammonium) N-(phosphonomethyl)glycine salt can be expressed as 7.4% a.e. by weight of N-(phosphonomethyl)glycine in its acid form.

"Biologically effective amount" means an amount necessary to produce an observable herbicidal effect on plant growth, including the effects of plant necrosis, plant death, growth inhibition, reproduction inhibition, inhibition of proliferation, and removal, destruction, or otherwise diminishing the occurrence and activity of plants.

"Suspoemulsion" means a liquid suspension containing both liquid particles and solid particles dispersed in a liquid continuous phase.

The term "combination" is intended to embrace application of each agent in a sequential manner in a regimen that will provide beneficial effects of the herbicide combination, and is intended as well to embrace compositions or co-administration of these agents in which the presence or application of these agents occurs in a substantially simultaneous manner, such as in a single spray mixture or treatment having a fixed ratio of these active agents.

b. Details

In accordance with the present invention, a combination comprising N-(phosphonomethyl)glycine (glyphosate) acid or a salt thereof and a triazolinone herbicide is now disclosed.

It is contemplated that in the present invention, N-(phosphonomethyl)glycine (formula (I)) can be present either in its acid form, in a salt form, including a zwitterion. If N-(phosphonomethyl)glycine is present in a salt form, preferably it is as a water-soluble salt. Some salts of N-(phosphonomethyl)glycine useful in the present invention are described in U.S. Pat. No. 3,799,758, herein incorporated by reference. Additional salts of N-(phosphonomethyl) glycine useful in the present invention are described in U.S. Pat. No. 4,405,531, herein incorporated by reference.

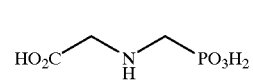

(I)

For example, N-(phosphonomethyl)glycine can be employed in the present invention as an alkali metal salt. Such alkali metal salts can include lithium, sodium, potassium, cesium, and rubidium salts. N-(phosphonomethyl)glycine can also be present in the composition of the instant invention as an alkaline earth metal salt. Such alkaline earth metal salts can comprise beryllium, magnesium, calcium, strontium, and barium salts. N-(Phosphonomethyl)glycine can be used as a mono-, di-, or tri- salt, for example, mono-, di-, or trisodium salts and mono-, di-, or tripotassium salts.

N-(Phosphonomethyl)glycine can further be used in the present combination as an organic ammonium salt. Such organic ammonium salts can comprise aliphatic or aromatic ammonium salts and can include primary, secondary, tertiary, or quaternary ammonium salts. Representative examples of such organic ammonium salts include, without limitation, methyl ammonium, ethylammonium, n-propylammonium, isopropylammonium, n-butylammonium, isobutylammonium, dodecylammonium, dimethylammonium, ethylmethylammonium, diethylammonium, trimethylammonium, dimethylstyrylammonium, dibutyldimethylammonium, tetramethylammonium, tetrabutylammonium, anilinium, pyridinium, morpholinium, 2-hydroxyethylammonium, di(hydroxyethyl)ammonium, N-ethoxylated tallowammonium, and allylammonium salts, and combinations thereof. The organic ammonium salts can be mono-, di-, or tri-salts such as, for example, mono (isopropylammonium) salts, di(isopropylammonium) salts, or tri(isopropylammonium) salts.

Additionally, N-(phosphonomethyl)glycine can be used in the combination of the instant invention as a salt of an inorganic cation such as a mono-, di-, or triammonium salt. Alternatively, N-(phosphonomethyl)glycine can be present as a sulfonium salt such as a mono-, di-, or tri (trimethylsulfonium) salt.

In the present composition, N-(phosphonomethyl)glycine can be neutralized with a base to form salts described in U.S. Pat. No. 4,405,531. The molar ratio of N-(phosphonomethyl)glycine to base can vary widely. For example, N-(phosphonomethyl)glycine and the base can be in a 1:1 molar ratio. When the base is isopropylamine, a 1:1 molar ratio of N-(phosphonomethyl)glycine to isopropylamine results in the formation of a mono (isopropylammonium) salt of N-(phosphonomethyl)glycine. When a 1:1.5 molar ratio is used, the result is a sesqui (isopropylammonium) salt; a 1:2 molar ratio results in a di(isopropylammonium) salt; a 1:3 molar ratio results in a tri(isopropylammonium) salt. The base can also be present in large excess above a 1:3 molar ratio of N-(phosphonomethyl)glycine to base.

Some triazolinone herbicides useful in the present invention are described generally in U.S. Pat. No. 5,125,958, herein incorporated by reference. Additional triazolinone herbicides useful in the present invention are described generally in U.S. Pat. No. 5,217,520, herein incorporated by reference. Still other triazolinone herbicides useful in the present invention are described generally in U.S. Pat. No. 4,818,275, herein incorporated by reference. The triazolinone herbicide can have a structure as shown in formula (II):

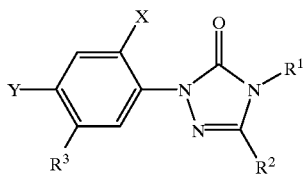

(II)

or a tautomer thereof, wherein:
R$^1$ is haloalkyl;
R$^2$ is halogen or lower alkyl;
R$^3$ is —CH$_2$CHClCO$_2$R$^4$ or —NHSO$_2$R$^5$;
R$^4$ is alkyl, alkoxycarbonylalkyl, cycloalkyl, benzyl, chlorobenzyl, alkylbenzyl, or haloalkylbenzyl;
R$^5$ is alkyl, haloalkyl, dialkylamino, carboxymethyl, hydroxy, or aryl;
X is hydrogen, halogen, alkyl, alkoxy, haloalkyl, or nitro; and
Y is hydrogen, halogen, alkyl, alkoxy, haloalkyl, haloloweralkylsulfinyl, or haloloweralkoxy.

R$^1$ is preferably difluoromethyl. R$^2$ is preferably lower alkyl, more preferably C$_1$ to about C$_5$ alkyl, and more preferably still it is methyl. Preferably R$^4$ is alkyl or alkoxy, more preferably R$^4$ is alkyl, still more preferably R4 is C$_1$ to about C$_5$ alkyl, and more preferably still R$^4$ is ethyl. R$^5$ is preferably alkyl, more preferably C$_1$ to about C$_5$ alkyl, and still more preferably R$^5$ is methyl. X is preferably a halogen and more preferably X is fluoro or chloro. Y is preferably a halogen and more preferably Y is chloro. When R$^3$ is —CH$_2$CHClCO$_2$R$^4$ then the triazolinone herbicide is a triazolinone acid ester herbicide. A particularly preferred triazolinone herbicide is carfentrazone-ethyl (formula (III)).

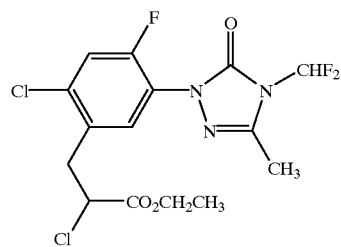

(III)

When R$^3$ is —NHSO$_2$R$^5$ then the triazolinone herbicide is a triazolinone sulfonamide herbicide. Another particularly preferred triazolinone herbicide is sulfentrazone (formula (IV)).

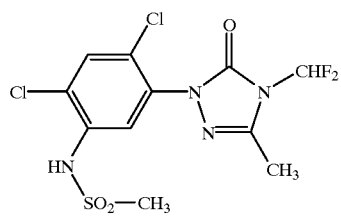

(IV)

The combination of the present invention can further comprise other ingredients. For example the combination can further comprise one or more surfactants or emulsifiers. Surfactants or emulsifiers which are useful in the present invention include without limitation an ethoxylated alkyl amine, an ethoxylated alkyl polyamine, an alkylpolyglucoside, an alkoxylated acetylenic diol, a polyoxyalkylene alkyl ether, an organosilicone, an ethoxylated alcohol, an ethoxylated Guerbet alcohol, an alkylphenol ethoxylate, a sulfated polyoxyalkylene alkylphenol, an alcohol sulfate, a polyoxyalkylene alcohol sulfate, a monoalcoholphosphate, a dialcoholphosphate, a mono (polyoxyalkylene alcohol)phosphate, a di(polyoxyalkylene alcohol)phosphate, a mono(polyoxyalkylene alkylphenol) phosphate, a di(polyoxyalkylene alkylphenol)phosphate, a polyoxyalkylene alkylphenol carboxylate, a polyoxyalkylene alcohol carboxylate, a fluorinated surfactant, a N-alkoxylated alkylpolyalkoxy amine surfactant (i.e., an etheramine surfactant), an alkylsulfonate, an alkylphenylsulfonate, an alkylsulfate, an alkylphenolsulfate, an alkyl betaine surfactant, an alkyl carboxylate (including fatty acids and fatty acid salts such as pelargonic acid), an ethoxylated alkylamide, a quaternary alkylamine, and combinations thereof. Preferred surfactants include an ethoxylated alkyl amine, an ethoxylated alkyl polyamine, an alkylpolyglucoside, a polyoxyalkylene alkyl ether, an ethoxylated alcohol, an ethoxylated Guerbet alcohol, a monoalcoholphosphate, a dialcoholphosphate, a mono (polyoxyalkylene alcohol)phosphate, a di(polyoxyalkylene alcohol)phosphate, a mono(polyoxyalkylene alkylphenol) phosphate, a di(polyoxyalkylene alkylphenol)phosphate, an etheramine surfactant, an alkyl betaine surfactant, a quaternary alkylamine, and combinations thereof. Still more preferred surfactants include an ethoxylated alkyl amine surfactant, an alkylpolyglucoside surfactant, an etheramine surfactant, a quaternary alkylamine surfactant, and combinations thereof. Ethoxylated alkyl amine surfactants such as a tallowamine ethoxylate are particularly preferred.

Alkoxylated acetylenic diol surfactants and polyoxyalkylene alkyl ether surfactants are also preferred in the combination of the present invention. Preferred alkoxylated acetylenic diols include polyethoxylated acetylenic diols, more preferably polyethoxylated tetramethyldecynediol, and still more preferably PEG-10 tetramethyldecynediol. PEG-10 tetramethyldecynediol is commercially available under the trade name Surfynol 465, available from Air Products and Chemicals, Inc. (Allentown, Pa., U.S.A.). Preferred polyoxyalkylene alkyl ethers include polyethoxyethylene-polyoxypropylene alkyl ethers, more preferably a polyethoxyethylene-polyoxypropylene-2-ethylhexyl ether such as Epan U-108 available from Dai-ichi Kogyo Seiyaku Co., Ltd. (Tokyo, Japan) or Newkalgen 4016EHB available from Takemoto Oil and Fat Co., Ltd. (Aichi, Japan). Typically the polyethoxyethylenepolyoxypropylene-2-ethylhexyl ether surfactant comprises about 5 to about 30, preferably about 10 to about 25, and more preferably about 10 to about 20 moles of ethylene oxide per mole of surfactant. Also, the polyethoxyethylenepolyoxypropylene-2-ethylhexyl ether surfactant comprises about 5 to about 30, preferably about 10 to about 25, and more preferably about 10 to about 20 moles of propylene oxide per mole of surfactant. A particularly preferred polyethoxyethylenepolyoxypropylene-2-ethylhexyl ether surfactant comprises about 15 moles of ethylene oxide and about 15 moles of propylene oxide per mole of surfactant.

The combination of the present invention can also comprise a solvent. The solvent can comprise an organic solvent such as an aromatic solvent. Useful aromatic solvents include benzene, toluene, o-xylene, m-xylene, p-xylene, mesitylene, naphthalene, bis (α-methylbenzyl)xylene, phenylxylylethane, and combinations thereof. Other useful solvents include substituted aromatic solvents such as chlorobenzene or ortho-dichlorobenzene. Alternatively, the solvent can comprise an aliphatic solvent such as paraffin oil. As another alternative, the solvent can comprise a phosphate solvent, preferably a triaryl phosphate or an alkyldiaryl phosphate. Particularly useful phosphate solvents include trixylenyl phosphate and 2-ethylhexyl diphenyl phosphate. Combinations of aromatic, aliphatic and phosphate solvents can also be successfully used in the present invention. Other solvents which can be used successfully in the present invention include N-methylpyrrolidone, dimethylformamide, polyvinylpyrrolidone, 4-butyrolactone, and fatty acid esters.

An inorganic or an organic carrier can be included in the combination of the present invention. Examples of useful inorganic carriers include clay (such as bentonite, montmorillonite, or attapulgite), silica, alumina, ammonium sulfate, and diatomaceous earth. Examples of useful organic carriers include cellulose, polyethylene glycol, paraffins, and fatty acid esters such as methyl oleate or tridecyl stearate.

In the present invention the weight ratio of the acid equivalent of N-(phosphonomethyl)glycine or salt thereof to triazolinone herbicide can vary depending on the weed species which is sought to be controlled and depending on the desired result. Typically the weight ratio of N-(phosphonomethyl)glycine a.e. to triazolinone herbicide can range from about 1:1 to about 100:1, preferably from about 2:1 to about 75:1, more preferably from about 5:1 to about 50:1, and more preferably still from about 10:1 to about 40:1.

The combination of the present invention can be formulated in a variety of ways. For example, it can be a composition comprising a wettable powder, a water dispersible granule, a tablet, a briquette, an oil-in-water emulsion, a water-in-oil emulsion, a dispersion in water, a dispersion in oil, a water-based flowable, a suspoemulsion, or others.

For example, a wettable powder composition can comprise N-(phosphonomethyl)glycine or a salt thereof, the triazolinone herbicide, a surfactant as described above, and optionally a solid carrier as described above. The wettable powder can further comprise other inert ingredients such as an anti-caking agent, a defoaming agent, a disintegration agent, a binder, a spreader, or other materials. One method of preparing the wettable powder can comprise mixing about 5 to about 85 parts by weight of a triazolinone herbicide such as carfentrazone-ethyl or sulfentrazone with about 1 to about 30 parts by weight of a surfactant such as tallowamine ethoxylate. An inert carrier (about 5 to about 85 parts by weight) such as silica or ammonium sulfate can be mixed, for example in a high-shear blender, with about 5 to about 85 parts by weight of the acid equivalent of powdered N-(phosphonomethyl)glycine or a powdered solid salt of N-(phosphonomethyl)glycine such as N-(phosphonomethyl) glycine monoammonium salt. The surfactant/triazolinone herbicide mixture can then be added to the powder mixture under high shear, resulting in a wettable powder. Other inert ingredients can optionally be added.

The combination of the present invention can also take the form of a composition comprising a water dispersible granule formulation or a water soluble granule formulation. For example, one can prepare a triazolinone herbicide dispersion by mixing about 1 to about 85 parts by weight (preferably about 1 to about 70 parts by weight, more preferably about 2 to about 50 parts by weight, and still more preferably about 2 to about 30 parts by weight) of the triazolinone herbicide such as carfentrazone-ethyl or sulfentrazone with about 1 to about 30 parts by weight (preferably about 1 to about 20 parts by weight and more preferably about 1 to about 10 parts by weight) of a surfactant such as an alkoxylated acetylenic diol surfactant or a polyoxyalkylene alkyl ether surfactant. Optionally the triazolinone herbicide dispersion can contain a solvent such as a phosphate solvent or an aromatic solvent. The triazolinone herbicide dispersion can be mixed, for example by kneading, with about 5 to about 85 parts by weight (preferably about 10 to about 70 parts by weight, more preferably about 10 to about 60 parts by weight, and still more preferably about 20 to about 45 parts by weight) of the acid equivalent of powdered N-(phosphonomethyl)glycine or with a powdered solid salt of N-(phosphonomethyl)glycine such as ammonium N-(phosphonomethyl)glycine salt such that the resulting mixture is a dough. Other inert ingredients such as ammonium sulfate, a spreading agent such an alkoxylated organosilicone surfactant, a defoaming agent, an extrusion aid, a binder, or an inorganic carrier such as silica can optionally be added. The dough can optionally be shaped, for example by extrusion or by molding, and dried to form the water dispersible granule formulation.

In a preferred embodiment of the present invention, a solid herbicidal composition comprises N-(phosphonomethyl)glycine or a salt thereof, a triazolinone herbicide, an alkoxylated acetylenic diol surfactant, and a polyoxyalkylene alkyl ether surfactant.

For example, the triazolinone herbicide can be dispersed in a mixture comprising the alkoxylated acetylenic diol surfactant, the polyoxyalkylene alkyl ether surfactant, an alkoxylated organosilicone surfactant, and a solvent such as a phosphate solvent. These ingredients can be further mixed with N-(phosphonomethyl)glycine or a salt thereof to form a dough. The weight ratio of N-(phosphonomethyl)glycine or salt thereof to the triazolinone herbicide can vary over a wide range. Typically the weight ratio of N-(phosphonomethyl)glycine or salt thereof expressed as an acid equivalent to the triazolinone herbicide can in the range of about 1:1 to about 100:1, preferably about 2:1 to about 75:1, more preferably about 5:1 to about 50:1, and still more preferably about 10:1 to about 40:1. Preferably the triazolinone herbicide is carfentrazone-ethyl or sulfentrazone. Optionally, the mixture in which the triazolinone herbicide is dispersed further comprises a second solvent such as an aromatic solvent or an aliphatic solvent. The solid herbicidal composition can further optionally comprise a carrier such as silica, alumina, clay, ammonium sulfate, or cellulose. A preferred carrier is ammonium sulfate. The composition can also comprise a nitrite scavenger such as sodium sulfite. The solid herbicidal composition can be prepared, for example, as a wettable powder or as a water dispersible granule.

The solid herbicidal composition can be prepared by the steps of first providing mixture comprising:
(i) a triazolinone herbicide;
(ii) an alkoxylated acetylenic diol surfactant; and
(iii) a polyoxyalkylene alkyl ether surfactant;
and second combining N-(phosphonomethyl)glycine or a salt thereof (preferably a water-soluble salt) with the mixture to form a dough. The combining step can be performed in any convenient mixing equipment, for example in a kneader or in a pan granulator. The alkoxylated acetylenic diol surfactant can be used in the composition of the present invention in a wide range of concentrations. Typically the alkoxylated acetylenic diol surfactant is present in a concentration of from about 1% by weight to about 15% by weight, preferably from about 1% by weight to about 10% by weight, and more preferably from about 2% by weight to about 8% by weight. Preferably the alkoxylated acetylenic diol is an ethoxylated acetylenic diol. The degree of ethoxylation in the ethoxylated acetylenic diol can vary widely, typically about 1 mole to about 50 moles of ethylene oxide per mole of surfactant, preferably about 3 mole to about 30 moles of ethylene oxide per mole of surfactant, and more preferably about 5 mole to about 20 moles of ethylene oxide per mole of surfactant. Preferably the alkoxylated acetylenic diol is an ethoxylated tetramethyldecynediol surfactant. An ethoxylated tetramethyldecynediol surfactant which is especially useful in the present invention is Surfynol 465, supplied by Air Products and Chemicals, Inc. (Allentown, Pa., U.S.A.)

The polyoxyalkylene alkyl ether surfactant useful in the present invention can also be present in the composition over a wide range of concentrations. Typically the polyoxyalkylene alkyl ether surfactant is present in a concentration of from about 1% by weight to about 15% by weight, preferably from about 2% by weight to about 10% by weight, and more preferably from about 2% by weight to about 8% by weight. Preferably the polyoxyalkylene alkyl ether surfactant is a polyoxyethylenepolyoxypropylene-2-ethylhexyl ether surfactant.

Optionally, the dispersion of the triazolinone herbicide can further comprise a solvent. The concentration of the solvent can vary over a wide range. For example, the solvent can be present in a concentration of up to about 10% by weight, preferably up to about 7% by weight, and more preferably up to about 5% by weight. The solvent can, for example, be an aromatic solvent, a polyoxylated trialkylphenyl ether solvent, an aliphatic solvent, a phosphate solvent, a polyarylalkyl solvent, or a solvent such as dimethylformamide, 4-butyrolactone, or N-methyl pyrrolidone. Examples of aromatic solvents include $C_9$ solvents such as o-xylene, m-xylene, p-xylene, and mixtures thereof. Other aromatic solvents useful in the present invention include phenylxylylethane or bis($\alpha$-methylbenzyl)xylene. Examples of the phosphate solvent include trixylenyl phosphate and 2-ethylhexyl diphenyl phosphate. Also optionally, the dispersion of the triazolinone herbicide can further comprise an alkoxylated organosilicone surfactant such as Silwet L-77 (available from OSi Specialties, Inc., Danbury, Conn., U.S.A.). The alkoxylated organosilicone surfactant, if present, can be in the composition in a wide range of concentrations, typically up to about 10% by weight, preferably up to about 7% by weight, and more preferably up to about 5% by weight. If a carrier is employed in the composition of the present invention, the carrier can typically be present in a concentration of up to 85% by weight, preferably up to about 80% by weight, and more preferably up to about 70% by weight. The dough can optionally be shaped (for example by extruding, molding, or pan granulation) and thereafter dried. The second step of combining the triazolinone dispersion with N-(phosphonomethyl)glycine can further comprise combining a carrier or a nitrite scavenger such as sodium sulfite.

The composition of the present invention can alternatively be prepared as a dispersion such as an emulsion. For example, the composition can comprise N-(phosphonomethyl)glycine or a salt thereof, and a triazolinone herbicide having the structure of formula (V):

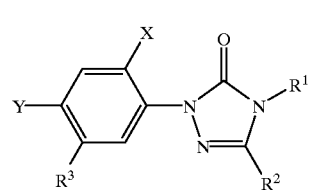

(V)

or a tautomer thereof, wherein:
$R^1$ is haloalkyl;
$R^2$ is selected from the group consisting of halogen and lower alkyl;
$R^3$ is selected from the group consisting of —$CH_2CHClCO_2R^6$ and —$NHSO_2R^5$;
$R^6$ is selected from the group consisting of H, alkyl, alkoxycarbonylalkyl, cycloalkyl, benzyl, chlorobenzyl, alkylbenzyl, and haloalkylbenzyl;
$R^5$ is selected from the group consisting of alkyl, haloalkyl, dialkylamino, carboxymethyl, hydroxy, and aryl;
X is selected from the group consisting of hydrogen, halogen, alkyl, alkoxy, haloalkyl, and nitro; and
Y is selected from the group consisting of hydrogen, halogen, alkyl, alkoxy, haloalkyl, halo lower alkylsulfinyl, and halo lower alkoxy;
and wherein the N-(phosphonomethyl)glycine or salt thereof is substantially dissolved in an aqueous phase and the triazolinone herbicide is substantially dissolved in a hydrophobic phase.

For example, a hydrophobic phase can be prepared comprising the triazolinone herbicide, and optionally a surfactant, and also optionally a solvent. An aqueous phase can be prepared comprising water, the N-(phosphonomethyl)glycine or salt thereof, and optionally a surfactant. The hydrophobic phase and the aqueous phase can be combined under shear, thereby producing the emulsion composition. The emulsion can be an oil-in-water emulsion or it can be a water-in-oil emulsion. Preferably the emulsion is an oil-in-water emulsion.

The ratio of N-(phosphonomethyl)glycine or salt thereof to triazolinone herbicide in the emulsion composition can vary over a wide range. Typically the ratio of N-(phosphonomethyl)glycine or salt thereof expressed on an acid equivalent basis to triazolinone herbicide is in the range of about 1:1 to about 100:1, preferably about 2:1 to about 75:1, more preferably about 5:1 to about 50:1, and still more preferably 10:1 to about 40:1.

By way of further example, in the emulsion composition of the present invention the triazolinone herbicide (about 0.5 to about 85 parts by weight, preferably about 1 to about 70 parts by weight, more preferably about 2 to about 50 parts by weight, and still more preferably about 2 to about 30 parts by weight) and, optionally, an emulsifier (about 0.5 to about 15 parts by weight) can be dispersed into a liquid comprising a solvent (about 10 to about 95 parts by weight, preferably about 20 to about 95 parts by weight) to form a hydrophobic solution. The solvent can, for example, comprise an aromatic solvent, a substituted aromatic solvent, an aliphatic solvent, a phosphate solvent, dimethylformamide, 4-butyrolactone, or N-methyl pyrrolidone. A preferred emulsifier can comprise, for example, an anionic surfactant, a cationic surfactant, or a nonionic surfactant. Preferably the emulsifier comprises an anionic surfactant. The anionic surfactant can comprise, for example, a phosphate ester, an alcohol ether sulfate, an alkylaryl ether sulfate, an alkylaryl sulfonate, a carboxylate, a naphthalene sulfonate, or a sulfosuccinate. A preferred surfactant is an alkylaryl sulfonate such as an alkylbenzenesulfonic acid salt. An anionic surfactant particularly useful in the present invention comprises an alkylbenzenesulfonic acid salt such as calcium dodecylbenzenesulfonate. The emulsifier can also comprise a nonionic surfactant. For example, the nonionic surfactant can comprise an alcohol ether, an alkoxylated alkylphenol resin, an alkoxylated vegetable oil, an alkylphenol ether, a block co-polymer, a fatty acid alkoxylate, a sorbitol alkoxylate, a sorbitan alkoxylates, a sorbitol ester, or a sorbitan ester. In a preferred embodiment, the emulsifier can also comprise a blend of emulsifiers such as a blend of an anionic surfactant and a nonionic surfactant.

Separately an aqueous solution comprising N-(phosphonomethyl)glycine or a salt thereof, such as mono(isopropylammonium) N-(phosphonomethyl)glycine or mono(2-hydroxyethylammonium) N-(phosphonomethyl)glycine (about 5 to about 85 parts by weight, preferably about 10 to about 70 parts by weight, more preferably about 10 to about 60 parts by weight, and still more preferably about 20 to about 45 parts by weight of N-(phosphonomethyl)glycine acid equivalent in about 20 to about 95 parts by weight of water), and, optionally, a surfactant (about 0.5 to about 15 parts by weight) can be prepared. Useful surfactants can have a variety of chemistries. For example, the surfactant can comprises a compound selected from the group consisting of an ethoxylated alkyl amine, an ethoxylated alkyl polyamine, an alkylpolyglucoside, an alkoxylated acetylenic diol, a polyoxyalkylene alkyl ether, an organosilicone, an ethoxylated alcohol, an ethoxylated Guerbet alcohol, an alkylphenol ethoxylate, a sulfated polyoxyalkylene alkylphenol, an alcohol sulfate, a polyoxyalkylene alcohol sulfate, a monoalcoholphosphate, a dialcoholphosphate, a mono(polyoxyalkylene alcohol)phosphate, a di(polyoxyalkylene alcohol)phosphate, a mono(polyoxyalkylene alkylphenol) phosphate, a di(polyoxyalkylene alkylphenol)phosphate, a polyoxyalkylene alkylphenol carboxylate, a polyoxyalkylene alcohol carboxylate, a fluorinated surfactant, a N-alkoxylated alkylpolyalkoxy amine surfactant (i.e. an etheramine surfactant), an alkylsulfonate, an alkylphenylsulfonate, an alkylsulfate, an alkylphenolsulfate, an alkyl betaine surfactant, an alkyl carboxylate (including a fatty acid or a fatty acid salt such as pelargonic acid), an ethoxylated alkylamide, a quaternary alkylamine, and combinations thereof. Preferred surfactants include an ethoxylated alkyl amine, an ethoxylated alkyl polyamine, an alkylpolyglucoside, a polyoxyalkylene alkyl ether, an ethoxylated alcohol, an ethoxylated Guerbet alcohol, a monoalcoholphosphate, a dialcoholphosphate, a mono(polyoxyalkylene alcohol)phosphate, a di(polyoxyalkylene alcohol)phosphate, a mono(polyoxyalkylene alkylphenol) phosphate, a di(polyoxyalkylene alkylphenol)phosphate, an etheramine surfactant, an alkyl betaine surfactant, a quaternary alkylamine, and combinations thereof. Still more preferred surfactants include an ethoxylated alkyl amine surfactant, an alkylpolyglucoside surfactant, an etheramine surfactant, a quaternary alkylamine surfactant, and combinations thereof. Ethoxylated alkyl amine surfactants such as a tallowamine ethoxylate are particularly preferred. The ethoxylated alkylamine surfactant can typically have an alkyl group containing from about 10 to about 30 carbon atoms, preferably from about 10 to about 25 carbon atoms, and more preferably from about 10 to about 20 carbon atoms. The ethoxylated alkylamine surfactant can typically have an average degree of ethoxylation ranging from about 1 to about 30 moles of ethylene oxide per mole of surfactant, preferably from about 5 to about 25 moles of ethylene oxide per mole of surfactant, and more preferably from about 10 to about 20 moles of ethylene oxide per mole of surfactant. Another particularly preferred surfactant is an etheramine surfactant. Preferred etheramine surfactants are described in U.S. Pat. No. 5,750,468, herein incorporated by reference. Etheramine surfactants especially useful in the present invention include those having the chemical structure:

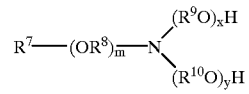

wherein $R^7$ is a moiety selected from the group consisting of about $C_6$ to about $C_{22}$ alkyl, aryl, and alkylaryl; m is an average number from about 1 to about 10; $R^8$ is alkylene having 1 to about 4 carbon atoms; $R^9$ and $R^{10}$ are independently alkylene groups having from 1 to about 4 carbon atoms; and x and y are average numbers such that the sum of x and y is in the range from about 2 to about 60. Preferably $R^7$ is about $C_8$ to about $C_{18}$ alkyl. $R^8$ is preferably ethylene, 1,3-propanediyl, or isopropylene, more preferably $R^8$ is ethylene or isopropylene. $R^9$ and $R^{10}$ are preferably both ethylene. Preferably m is from about 1 to about 5. Preferably the sum of x and y is from about 2 to about 20. Another etheramine surfactant useful in the present invention is an etheramine N-oxide surfactant. Yet another useful etheramine is one in which the N atom has been quaternized with a $C_1$ to about $C_4$ alkyl group.

The hydrophobic solution prepared as described above can be added to the aqueous solution, preferably under high shear (for example in a Waring blender or using a rotostator mixer), to produce the emulsion. To help stabilize the emulsion, an emulsion stabilizer such as a xanthan gum can be added to the emulsion or to a phase of the emulsion. As an alternative method to help stabilize the emulsion, a dry or pre-swelled emulsion stabilizer such as silica, colloidal silica, fumed silica, alumina, colloidal alumina, or fumed alumina (about 0.25 to about 15 parts by weight, preferably about 0.5 to about 10 parts by weight, more preferably about 1 to about 5 parts by weight of the solid stabilizing agent) optionally can be added to one or more of the solutions during the preparation of the composition. A useful fumed silica is an Aerosil fumed silica (available from Degussa Corp., Ridgefield Park, N.J., U.S.A.) such as Aerosil 200. The stabilizing agent can be added in the hydrophobic phase, in the aqueous phase, or in both the hydrophobic and aqueous phases. Optionally, the emulsion formulation can comprise other ingredients such as a spreading agent (e.g., a silicone surfactant), an antifreezing agent (e.g., ethylene glycol or propylene glycol), a defoamer (e.g., a silicone defoamer such as an ethoxylated silicone), or sodium sulfite. The emulsion can further comprise a biostat such as 1,2-benzisothiazolin-3-one. If a defoaming agent is used, preferably it is Mazu DF100S (available from PPG Industries/Specialty Chemicals, Gurnee, Ill., U.S.A.). The emulsion formulation can also comprise a spreading agent such as an alkoxylated silicone spreading agent. A preferred spreading agent is an ethoxylated silicone such as Silwet L-77 (available from Union Carbide).

In a preferred embodiment of the present invention, the composition is an emulsion comprising (a) an aqueous phase comprising the mono(isopropylammonium) salt of N-(phosphonomethyl)glycine), an ethoxylated alkylamine surfactant, sodium sulfite, propylene glycol, and water; and (b) an hydrophobic phase comprising carfentrazone-ethyl, an aromatic solvent, calcium dodecylbenzenesulfonate, a nonionic surfactant, and a silicone defoamer; and wherein the hydrophobic phase is dispersed in the aqueous phase to form an emulsion.

The composition of the present invention can also be prepared as a dilute aqueous mixture suitable, for example, for applying to plant foliage. In one embodiment, the solid herbicidal composition (about 0.5 to about 20 parts by weight) described above can be dispersed into water (about 80 to about 99.5 parts by weight) to form the dilute aqueous mixture. In another embodiment, the emulsion formulation (about 0.5 to about 20 parts by weight) described above can be dispersed into water (about 20 to about 99.5 parts by weight) to form the dilute aqueous mixture.

An alternative method of preparing a dilute aqueous mixture is to prepare a concentrated formulation of the triazolinone herbicide and separately prepare a concentrated formulation of N-(phosphonomethyl)glycine or a salt thereof. Then the concentrated triazolinone herbicide formulation and the N-(phosphonomethyl)glycine formulation can be mixed together with water or with another carrier or diluent. A triazolinone herbicide formulation useful for this application can for example comprise a triazolinone (such as carfentrazone-ethyl or sulfentrazone), a solvent, and a surfactant.

Specific examples of formulations are provided below in order to aid the reader in understanding the scope and utility of the present invention.

In another embodiment the present invention provides a method of treating plants wherein the method comprises contacting foliage of a plant with a biologically effective amount of a composition comprising N-(phosphonomethyl) glycine or a salt thereof, and a triazolinone herbicide such as that encompassed by formula (II), including carfentrazone-ethyl or sulfentrazone. The composition of the present invention should be applied to plants at a rate sufficient to give the desired biological effect. These application rates are usually expressed as amount of herbicide per unit area treated, e.g., grams of active ingredient or of acid equivalent per hectare (g/ha). What constitutes a "desired effect" varies according to the standards and practice of those who investigate, develop, market, and use a specific class of herbicides. For example, the amount of herbicide applied per unit area to give 85% control of a plant species as measured by growth reduction or mortality is often used to define a commercially effective rate.

Control of a plant species is one of the biological effects that that can be enhanced through this invention. "Control" as used herein refers to any observable measure of herbicidal effects on plant growth, which effects can include one or more of the effects of plant necrosis, plant death, growth inhibition, reproduction inhibition, inhibition of proliferation, and removal, destruction, or otherwise diminishing the occurrence and activity of plants.

The herbicidal effectiveness data set forth herein report "percent inhibition" as a percentage of control of a plant species relative to a set of untreated check plants. The measurement of inhibition and control reflects a standard procedure known to those of skill in the art and comprises a visual assessment of plant mortality and growth reduction by comparison with untreated plants, made by technicians specially trained to make and record such observations. A single technician makes all assessments of percent inhibition within any one experiment or trial.

The selection of application rates that are biologically effective for the composition of the present invention, including application rate in grams per hectare of each herbicide in the present composition, can be made by one of skill in the art given the present disclosure. Considerations in determining the application rate include individual plant conditions, weather, and growing conditions.

The combination of the present invention can be applied to the plants, for example, as a liquid spray. In one embodiment, the combination can be prepared as a liquid or a solid composition which can be dispersed into water and applied onto the foliage of plants. Alternatively, the present combination can be prepared as a concentrated liquid which can be directly applied to plant foliage, for example through a controlled droplet applicator. In another alternative, the combination can be directly prepared as a dilute liquid which can be applied to plant foliage. Common application methods include spraying and wiping.

The combination of the present invention can be used to control a wide variety of plants worldwide. The combination can be applied to a plant in a herbicidally effective amount and can effectively control one or more plant species in a large variety of plant genera. Table 1 lists some examples, without limitation, of common plant genera containing species which can be controlled by the present combination.

TABLE 1

| Genus |
| --- |
| Abutilon |
| Amaranthus |
| Artemisia |
| Asclepias |
| Avena |

TABLE 1-continued

| Genus |
| --- |
| Axonopus |
| Borreria |
| Brachiaria |
| Brassica |
| Bromus |
| Chenopodium |
| Cirsium |
| Commelina |
| Convolvulus |
| Cynodon |
| Cyperus |
| Digitaria |
| Ipomoea |
| Kochia |
| Lolium |
| Malva |
| Oryza |
| Ottochloa |
| Panicum |
| Paspalum |
| Phalaris |
| Phragmites |
| Polygonum |
| Portulaca |
| Pteridium |
| Pueraria |
| Rubus |
| Salsola |
| Setaria |
| Sida |
| Sinapis |
| Sorghum |
| Triticum |
| Typha |
| Ulex |
| Xanthium |
| Zea |

Table 2 lists some important plant species which the present invention can control. This list is not meant to be limiting and one of skill in the art will recognize given the present disclosure that a large number of additional species can be controlled with the present invention.

TABLE 2

| Common Name | Scientific Name |
| --- | --- |
| velvetleaf | Abutilon theophrasti |
| pigweed | Amaranthus spp. |
| buttonweed | Borreria spp. |
| oilseed rape, canola, indian mustard, etc. | Brassica spp. |
| common lambsquarter | Chenopodium album |
| commelina | Commelina spp. |
| filaree | Erodium spp. |
| sunflower | Helianthus spp. |
| morningglory | Ipomoea spp. |
| kochia | Kochia scoparia |
| mallow | Malva spp. |
| wild buckwheat, smartweed, etc. | Polygonum spp. |
| purslane | Portulaca spp. |
| russian thistle | Salsola spp. |
| sida | Sida spp. |
| wild mustard | Sinapis arvensis |
| cocklebur | Xanthium spp. |
| wild oat | Avena fatua |
| carpetgrass | Axonopus spp. |
| downy brome | Bromus tectorum |
| crabgrass | Digitaria spp. |
| barnyardgrass | Echinochloa crus-galli |
| goosegrass | Eleusine indica |
| Annual ryegrass | Lolium multiflorum |
| rice | Oryza sativa |
| ottochloa | Ottochloa nodosa |
| bahiagrass | Paspalum notatum |
| canarygrass | Phalaris spp. |
| foxtail | Setaria spp. |
| wheat | Triticum aestivum |
| corn | Zea mays |
| mugwort | Artemisia spp. |
| milkweed | Asclepias spp. |
| Canada thistle | Cirsium arvense |
| field bindweed | Convolvulus arvensis |
| kudzu | Pueraria spp. |
| brachiaria | Brachiaria spp. |
| bermudagrass | Cynodon dactylon |
| yellow nutsedge | Cyperus esculentus |
| purple nutsedge | Cyperus rotundus |
| quackgrass or couch | Elymus repens |
| lalang | Imperata cylindrica |
| perennial ryegrass | Lolium perenne |
| guineagrass | Panicum maximum |
| dallisgrass | Paspalum dilatatum |
| reed | Phragmites spp. |
| johnsongrass | Sorghum halepense |
| cattail | Typha spp. |
| horsetail | Equisetum spp. |
| bracken | Pteridium aquilinum |
| blackberry | Rubus spp. |
| gorse | Ulex europaeus | c. Detailed Methods

The starting materials for use in preparing the composition and for performing the methods of the invention are known or can be prepared by conventional methods known to a skilled person or in an analogous manner to processes described in the art.

Generally, the process methods of the present invention can be performed as follows.

EXAMPLE 1

Water Soluble Granule a. Preparation of Carfentrazone-ethyl Solution

Charge a 2 liter vessel with 62.5 g of technical grade carfentrazone-ethyl, 385 g of polyoxyethylenepolyoxypropylene-2-ethylhexyl ether (Newkalgen 4016EHB, comprising about 15 moles of ethylene oxide and about 15 moles of propylene oxide per mole of surfactant, available from Takemoto Oil and Fat Co. Ltd., Gamagori, Aichi 443, Japan), 220.5 g of Silwet L-77 (an organosilicone surfactant available from OSi Specialties, Inc., Danbury, Conn., U.S.A.), 166 g of Surfynol 465 (a alkoxylated acetylenic diol surfactant available from Air Products, Inc., Allentown, Pa., U.S.A.), and 166 g of trixylenyl phosphate. Gently heat the vessel in a water bath. Stir the mixture for about 30 minutes at about 80° C.

b. Preparation of Granular Formulation

Mix the carfentrazone-ethyl solution with 1280 g of 86% by weight (acid equivalent) monoammonium salt of N-(phosphonomethyl)glycine and 2720 g of ammonium sulfate, in a kneader. Mix the mixture with 150 g of water for about 10 minutes at room temperature. Knead the mixture for about 30 minutes to make an extrudable dough. Extrude the dough through a screen having 1 mm openings, intended for lateral (radial) extrusion. Dry the resulting granules using an electric fan dryer at 70° C. for one hour. The composition of the final granule will be as follows:

| Ingredient | Weight Percent |
| --- | --- |
| carfentrazone-ethyl | 1.25 |
| polyoxyethylenepolyoxypropylene-2-ethylhexyl ether | 7.70 |
| Silwet L-77 | 4.41 |
| Surfynol 465 | 3.32 |
| trixylenyl phosphate | 3.32 |
| monoammonium glyphosate (86% a.e.*) | 25.60 (22.00 a.e.) |
| ammonium sulfate powder | 54.40 |

*a.e. = acid equivalent

EXAMPLE 2

Water Soluble Granule a. Preparation of Carfentrazone-ethyl Solution

Charge a 2 liter vessel with 103.5 g of technical grade carfentrazone-ethyl, 332.5 g of polyoxyethylenepolyoxypropylene-2-ethylhexyl ether (Newkalgen 4016EHB, comprising about 15 moles of ethylene oxide and about 15 moles of propylene oxide per mole of surfactant), 47.5 g of Silwet L-77, 379 g of Surfynol 465, 190 g of trixylenyl phosphate, 24 g of phenylxylylethane, 21.5 g of bis(α-methylbenzyl)xylene, and 2 g of xylene based solvents. Gently heat the vessel in a water bath. Stir the mixture for about 30 minutes at about 80° C.

b. Preparation of Granular Formulation

Mix the carfentrazone-ethyl solution with 2100 g of 86% by weight (acid equivalent) monoammonium salt of N-(phosphonomethyl)glycine and 1800 g of ammonium sulfate, in a kneader. Mix the mixture with 150 g of water for about 10 minutes at room temperature. Knead the mixture for about 30 minutes to make an extrudable dough. Extrude the dough through a screen having 1 mm openings, intended for lateral (radial) extrusion. Dry the resulting granules using an electric fan dryer at 70° C. for one hour. The composition of the final granule will be as follows:

| Ingredient | Weight Percent |
| --- | --- |
| carfentrazone-ethyl | 2.07 |
| polyoxyethylenepolyoxypropylene-2-ethylhexyl ether | 6.65 |
| Silwet L-77 | 0.95 |
| Surfynol 465 | 7.58 |
| trixylenyl phosphate | 3.8 |
| phenylxylylethane | 0.48 |
| bis(α-methylbenzyl)xylene | 0.43 |
| xylene based solvents | 0.04 |
| monoammonium glyphosate (86% a.e.) | 42.00 (36.12 a.e.) |
| ammnonium sulfate powder | 36.00 |

EXAMPLE 3

Water Soluble Granule a. Preparation of Carfentrazone-ethyl Solution

Charge a 2 liter vessel with 62.5 g of technical grade carfentrazone-ethyl, 385 g of polyoxyethylenepolyoxypropylene-2-ethylhexyl ether (Newkalgen 4016EHB, comprising about 15 moles of ethylene oxide and about 15 moles of propylene oxide per mole of surfactant), 220.5 g of Silwet L-77, 166 g of Surfynol 465, and 166 g of trixylenyl phosphate. Gently heat the vessel in a water bath. Stir the mixture for about 30 minutes at about 80° C.

b. Preparation of Granular Formulation

Mix the carfentrazone-ethyl solution with 2100 g of 86% by weight (acid equivalent) monoammonium salt of N-(phosphonomethyl)glycine and 1900 g of ammonium sulfate, in a kneader. Mix the mixture with 150 g of water for about 10 minutes at room temperature. Knead the mixture for about 30 minutes to make an extrudable dough. Extrude the dough through a screen having 1 mm openings, intended for lateral (radial) extrusion. Dry the resulting granules using an electric fan dryer at 70° C. for one hour. The composition of the final granule will be as follows:

| Ingredient | Weight Percent |
| --- | --- |
| carfentrazone-ethyl | 1.25 |
| polyoxyethylenepolyoxypropylene-2-ethylhexyl ether | 7.70 |
| Silwet L-77 | 4.41 |
| Surfynol 465 | 3.32 |
| trixylenyl phosphate | 3.32 |
| monoammonium glyphosate (86% a.e.) | 42.00 (36.12 a.e.) |
| ammonium sulfate powder | 38.00 |

EXAMPLE 4

Water Soluble Granule a. Preparation of Carfentrazone-ethyl Solution

Charge a 2 liter vessel with 62.5 g of technical grade carfentrazone-ethyl, 385 g of polyoxyethylenepolyoxypropylene-2-ethylhexyl ether (Newkalgen 4016EHB, comprising about 15 moles of ethylene oxide and about 15 moles of propylene oxide per mole of surfactant), 220.5 g of Silwet L-77, 166 g of Surfynol 465, and 166 g of trixylenyl phosphate. Gently heat the vessel in a water bath. Stir the mixture for about 30 minutes at about 80° C.

b. Preparation of Granular Formulation

Mix the carfentrazone-ethyl solution with 4000 g of 86% by weight (acid equivalent) monoammonium salt of N-(phosphonomethyl)glycine, in a kneader. Mix the mixture with 150 g of water for about 10 minutes at room temperature. Knead the mixture for about 30 minutes to make an extrudable dough. Extrude the dough through a screen having 1 mm openings, intended for lateral (radial) extrusion. Dry the resulting granules using an electric fan dryer at 70° C. for one hour. The composition of the final granule will be as follows:

| Ingredient | Weight Percent |
| --- | --- |
| carfentrazone-ethyl | 1.25 |
| polyoxyethylenepolyoxypropylene-2-ethylhexyl ether | 7.70 |
| Silwet L-77 | 4.41 |
| Surfynol 465 | 3.32 |
| trixylenyl phosphate | 3.32 |

-continued

| Ingredient | Weight Percent |
| --- | --- |
| monoammonium glyphosate (86% a.e.) powder | 80.00 (68.8 a.e.) |

EXAMPLE 5

Water Soluble Granule a. Preparation of Carfentrazone-ethyl Solution

Charge a 2 liter vessel with 101 g of technical grade carfentrazone-ethyl, 330 g of polyoxyethylenepolyoxypropylene-2-ethylhexyl ether (Newkalgen 4016EHB, comprising about 15 moles of ethylene oxide and about 15 moles of propylene oxide per mole of surfactant), 47.5 g of Silwet L-77, 375 g of Surfynol 465, 47.5 g of xylene based solvent mix, and 190 g of 2-ethylhexyl diphenyl phosphate. Gently heat the vessel in a water bath. Stir the mixture for about 30 minutes at about 80° C.

b. Preparation of Granular Formulation

Mix the carfentrazone-ethyl solution with 2117.5 g of 86% by weight (acid equivalent) monoammonium salt of N-(phosphonomethyl)glycine and 1766.5 g of ammonium sulfate, in a kneader. Mix the mixture with 150 g of water for about 10 minutes at room temperature. Knead the mixture for about 30 minutes to make an extrudable dough. Extrude the dough through a screen having 1 mm openings, intended for lateral (radial) extrusion. Dry the resulting granules using an electric fan dryer at 70° C. for one hour. The composition of the final granule will be as follows:

| Ingredient | Weight Percent |
| --- | --- |
| carfentrazone-ethyl | 2.02 |
| polyoxyethylenepolyoxypropylene-2-ethylhexyl ether | 6.60 |
| Silwet L-77 | 0.95 |
| Surfynol 465 | 7.50 |
| xylene based solvent mix | 0.95 |
| 2-ethylhexyl diphenyl phosphate | 3.80 |
| monoammonium glyphosate (85% a.e.) | 42.35 (36.00 a.e.) |
| ammonium sulfate powder | 35.33 |
| water | 0.50 |

EXAMPLE 6

Water Soluble Granule a. Preparation of Carfentrazone-ethyl Solution

A 4 liter vessel is charged with 64 g of technical grade carfentrazone-ethyl, 560 g of polyoxyethylenepolyoxypropylene-2-ethylhexyl ether (Newkalgen 4016EHB, comprising about 15 moles of ethylene oxide and about 15 moles of propylene oxide per mole of surfactant), 40 g of Epan U-108 (a polyoxyethylenepolyoxypropylene ether nonionic surfactant available from Dai-Ichi Kogyo Seiyaku Co., Ltd., Tokyo, Japan), 40 g of Silwet L-77, 320 g of Surfynol 465, 40 g of Sorpol 7537 (a solvent from Toho Chemical Industries, Tokyo, Japan), and 240 g of 2-ethylhexyl diphenyl phosphate (available from Monsanto Company, St. Louis, Mo., U.S.A.). The vessel is gently heated in a water bath. The mixture is stirred for about 30 minutes at about 80° C.

b. Preparation of Granular Formulation

The carfentrazone-ethyl solution is mixed with 2176 g of 94% by weight (acid equivalent) monoammonium salt of N-(phosphonomethyl)glycine, 4216 g of ammonium sulfate, and 24 g of Emul 10 powder (sodium lauryl sulfate, available from Kao Corp., Tokyo, Japan) in a kneader. The mixture is mixed with 250 g of water for about 10 minutes at room temperature. The mixture is kneaded for about 30 minutes to make an extrudable dough. The dough is extruded through a screen having 1 mm openings, intended for lateral (radial) extrusion. The resulting granules are dried using an electric fan dryer at 70° C. for one hour. The composition of the final granule is as follows:

| Ingredient | Weight Percent |
| --- | --- |
| carfentrazone-ethyl | 0.80 |
| polyoxyethylenepolyoxypropylene-2-ethylhexyl ether | 6.60 |
| Sorpol 7537 | 4.00 |
| Silwet L-77 | 0.50 |
| Surfynol 465 | 4.00 |
| 2-ethylhexyl diphenyl phosphate | 3.00 |
| Epan U-108 | 0.50 |
| monoammonium glyphosate (94% a.e.) | 27.20 (25.57 a.e.) |
| ammonium sulfate powder | 52.7 |
| Emul 10 Powder | 0.30 |

EXAMPLE 7

Water Soluble Granule a. Preparation of Carfentrazone-ethyl Solution

A 20 mL beaker was charged with 1.25 g of technical grade carfentrazone-ethyl, 5.0 g of polyoxyethylenepolyoxypropylene-2-ethylhexyl ether (Newkalgen 4016EHB, comprising about 15 moles of ethylene oxide and about 15 moles of propylene oxide per mole of surfactant) and 3.0 g of Surfynol 465 (a alkoxylated acetylenic diol surfactant available from Air Products, Inc., Allentown, Pa., U.S.A.). The vessel was gently heated in a water bath. The mixture was stirred by hand for about 10 minutes at about 80° C.

b. Preparation of Granular Formulation

The carfentrazone-ethyl solution was mixed with 25.6 g of 86% by weight (acid equivalent) monoammonium salt of N-(phosphonomethyl)glycine and 65.15 g of ammonium sulfate, in a mortar. The mixture was mixed with 7.0 g of water for about 5 minutes by hand at room temperature. The mixture was kneaded for about 10 minutes by hand to make an extrudable dough. The dough was extruded through a screen having 1 mm openings, intended for lateral (radial) extrusion. The resulting granules were dried using an electric fan dryer at 70° C. for one hour. The composition of the final granule was as follows:

| Ingredient | Weight Percent |
| --- | --- |
| carfentrazone-ethyl | 1.25 |
| polyoxyethylenepolyoxypropylene-2-ethylhexyl ether | 5.00 |
| Surfynol 465 | 3.00 |

-continued

| Ingredient | Weight Percent |
| --- | --- |
| monoammonium glyphosate (86% a.e.) | 25.60 (22.00 a.e.) |
| ammonium sulfate powder | 65.15 |
| kneading water | 7.00 |

EXAMPLE 8

Water Soluble Granule a. Preparation of Carfentrazone-ethyl Solution

A 20 mL beaker was charged with 1.25 g of technical grade carfentrazone-ethyl, 5.0 g of polyoxyethylenepolyoxypropylene-2-ethylhexyl ether (Newkalgen 4016EHB, comprising about 15 moles of ethylene oxide and about 15 moles of propylene oxide per mole of surfactant), 0.5 g of Silwet L-77, 3.0 g of Surfynol 465, and 1.0 g of Takemoto 98122TX (polyoxyethylene(4 moles)-2,4,6-tristyrylphenyl ether of Takemoto Oil & Fat Ind. Co. Ltd., Japan). The beaker was gently heated in a water bath. The mixture was stirred by hand for about 5 minutes at about 80° C.

b. Preparation of Granular Formulation

The carfentrazone-ethyl solution was mixed with 25.6 g of 86% by weight (acid equivalent) monoammonium salt of N-(phosphonomethyl)glycine and 63.65 g of ammonium sulfate, in a mortar. The mixture was mixed with 7.0 g of water for about 5 minutes by hand at room temperature. The mixture was kneaded for about 5 minutes by hand to make an extrudable dough. The dough was extruded through a screen having 1 mm openings, intended for lateral (radial) extrusion. The resulting granules were dried using an electric fan dryer at 70° C. for one hour. The composition of the final granule was as follows:

| Ingredient | Weight Percent |
| --- | --- |
| carfentrazone-ethyl | 1.25 |
| polyoxyethylenepolyoxy propylene-2-ethylhexyl ether | 5.00 |
| Surfynol 465 | 3.00 |
| Silwet L-77 | 0.50 |
| polyoxyethylene-2,4,6-tristyrylphenyl ether | 1.00 |
| monoammonium glyphosate (86% a.e.*) | 25.60 (22.00 a.e.) |
| ammonium sulfate powder | 63.65 |
| kneading water | 7.00 |

EXAMPLE 9

Water Soluble Granule a. Preparation of Carfentrazone-ethyl Solution

A 20 mL beaker was charged with 1.25 g of technical grade carfentrazone-ethyl, 5.0 g of polyoxyethylenepolyoxypropylene-2-ethylhexyl ether (Newkalgen 4016EHB, comprising about 15 moles of ethylene oxide and about 15 moles of propylene oxide per mole of surfactant), 3.0 g of Surfynol 465, and 1.0 g of alkylbenzene derivative solvent. The beaker was gently heated in a water bath. The mixture was stirred by hand for about 5 minutes at about 80° C.

b. Preparation of Granular Formulation

The carfentrazone-ethyl solution was mixed with 25.6 g of 86% by weight (acid equivalent) monoammonium salt of N-(phosphonomethyl)glycine and 64.15 g of ammonium sulfate, in a mortar. The mixture was mixed with 7.0 g of water for about 5 minutes by hand at room temperature. The mixture was kneaded for about 5 minutes by hand to make an extrudable dough. The dough was extruded through a screen having 1 mm openings, intended for lateral (radial) extrusion. The resulting granules were dried using an electric fan dryer at 70° C. for one hour. The composition of the final granule was as follows:

| Ingredient | Weight Percent |
| --- | --- |
| carfentrazone-ethyl | 1.25 |
| polyoxyethylenepolyoxy propylene-2-ethylhexyl ether | 5.00 |
| Surfynol 465 | 3.00 |
| alkylbenzene derivative solvent | 1.00 |
| monoammonium glyphosate (86% a.e.*) | 25.60 (22.00 a.e.) |
| ammonium sulfate powder | 64.15 |
| kneading water | 7.00 |

EXAMPLE 10

Emulsion Formulation a. Carfentrazone-ethyl Pre-mix

Add 2.92 g of 95% carfentrazone-ethyl to 6.00 g of Aromatic 200 solvent (a $C_9$ aromatic solvent blend having a flashpoint of greater than 93° C., and sold by Exxon Corp., Houston, Tex., U.S.A.). Add to this mixture 2.00 g of Armul 1496 HF (a surfactant blend available from Witco Corp., Perth Amboy, N.J., U.S.A.) and 2.00 g Armul 1505 HF (a surfactant blend available from Witco Corp.). Mix until homogeneous.

b. Mono(isopropylammonium)N-(phosphonomethyl) glycine Pre-mix

To 26.36 g of deionized water add 42.52 g of a 45.72% a.e. aqueous solution of mono(isopropylammonium) N-(phosphonomethyl)glycine (available from Monsanto Company, St. Louis, Mo., U.S.A.). Add to this mixture 10.00 grams of Ethomeen T/25 (ethoxylated tallowamine, available from Akzo Chemicals Inc., Chicago, Ill., U.S.A.), 0.10 g of sodium sulfite, 2.00 grams of propylene glycol, and 0.10 g of silicone defoamer (such as Sag 30, available from OSi Specialties, Inc., Danbury, Conn., U.S.A.). Mix until homogeneous.

c. Xanthan Gum Premix

To 5.82 grams of deionized water add 0.06 g of Kelzan S (xanthan gum, available from Kelco, Inc., San Diego, Calif., U.S.A.) and 0.12 g of Proxel GXL (1,2-benzisothiazolin-3-one solution available as a biostat from ICI Americas, Inc., Wilmington, Del., U.S.A.). Mix, for example in a blender or using a rotostator mixer, until homogeneous.

d. Emulsion

Agitate the mono(isopropylammonium) N-(phosphonomethyl)glycine pre-mix under high shear and to it slowly add the carfentrazone-ethyl premix. Continue mixing for about five minutes. Then add the xanthan gum premix to the stirred mixture. Continue mixing gently until homogeneous. The resulting mixture will be an emulsion formulation of mono(isopropylammonium)

N-(phosphonomethyl)glycine and carfentrazone-ethyl. The final composition of the emulsion will be as follows:

| Ingredient | Weight Percent |
|---|---|
| carfentrazone-ethyl (95%) | 2.92 |
| Armul 1496 HF | 2.00 |
| Armul 1505 HF | 2.00 |
| Aromatic 200 | 6.00 |
| mono(isopropylammonium) glyphosate (45.72% a.e.) | 42.52 (19.44 a.e.) |
| Ethomeen T/25 | 10.00 |
| sodium sulfite | 0.10 |
| propylene glycol | 2.00 |
| silicone defoamer | 0.10 |
| Kelzan S | 0.06 |
| Proxel GXL | 0.12 |
| water | 32.18 |

EXAMPLE 11

Emulsion Formulation a. Carfentrazone-ethyl Pre-mix

Add 2.45 g of 95% carfentrazone-ethyl to 25.00 g of Aromatic 200 solvent (a $C_9$ aromatic solvent blend having a flashpoint of greater than 93° C., and sold by Exxon Corp., Houston, Tex., U.S.A.). Add to this mixture 5.00 g of Armul 1496/1505HF (an calcium dodecylbenzene sulfonate/nonionic surfactant blend available from witco Corp., Perth Amboy, N.J., U.S.A.). Further add to this mixture 0.1 g of Mazu 100DS (a silicone defoamer available from PPG Industries/Specialty Chemicals, Gurnee, Ill., U.S.A.). Next add 2.00 g of Aerosil 200 fumed silica (available from Degussa Corp., Ridgefield Park, N.J., U.S.A.). Mix under high shear (for example, in a Waring blender) until homogeneous.

b. Mono(isopropylammonium)N-(phosphonomethyl)glycine Pre-mix

To 18.30 g of deionized water add 36.05 g of a 45.72% a.e. aqueous solution of mono(isopropylammonium) N-(phosphonomethyl)glycine (available from Monsanto Company, St. Louis, Mo., U.S.A.). Add to this mixture 10.00 grams of Ethomeen T/25 (tallowamine 15-mole ethoxylate, available from Akzo Chemicals Inc., Chicago, Ill., U.S.A.), and 0.10 g of sodium sulfite, 1.00 grams of propylene glycol. Mix until homogeneous.

c. Emulsion

Agitate the mono(isopropylammonium) N-(phosphonomethyl)glycine pre-mix under high shear (for example, in a Waring blender) and to it slowly add the carfentrazone-ethyl premix. Continue mixing for about five minutes. Continue mixing gently until homogeneous. The resulting mixture will be an emulsion formulation of mono (isopropylammonium) N-(phosphonomethyl)glycine and carfentrazone-ethyl. The final composition of the emulsion will be as follows:

| Ingredient | Weight Percent |
|---|---|
| carfentrazone-ethyl (95%) | 2.45 |
| Armul 1496/1505 HF | 5.00 |
| Aromatic 200 | 25.00 |
| mono(isopropylammonium) glyphosate (45.72% a.e.) | 36.05 (16.48 a.e.) |
| Ethomeen T/25 | 10.00 |
| sodium sulfite | 0.10 |
| propylene glycol | 1.00 |
| Mazu 100DS silicone defoamer | 0.10 |
| fumed silica | 2.00 |
| deionized water | 18.30 |

EXAMPLE 12

Emulsion Formulation a. Carfentrazone-ethyl Pre-mix

Add 2.45 g of 95% carfentrazone-ethyl to 25.00 g of Aromatic 200 solvent (a $C_9$ aromatic solvent blend having a flashpoint of greater than 93° C., and sold by Exxon Corp., Houston, Tex., U.S.A.). Add to this mixture 5.00 g of Armul 1496/1505HF (an calcium dodecylbenzene sulfonate/nonionic surfactant blend available from Witco Corp., Perth Amboy, N.J., U.S.A.). Further add to this mixture 0.1 g of Mazu 100DS (a silicone defoamer available from PPG Industries/Specialty Chemicals, Gurnee, Ill., U.S.A.). Next add 2.00 g of Aerosil 200 fumed silica (available from Degussa Corp., Ridgefield Park, N.J., U.S.A.). Mix under high shear (for example, in a Waring blender) until homogeneous.

b. Mono(isopropylammonium) N-(phosphonomethyl)glycine Pre-mix

To 18.30 g of deionized water add 36.05 g of a 45.72% a.e. aqueous solution of mono(isopropylammonium) N-(phosphonomethyl)glycine (available from Monsanto Company, St. Louis, Mo., U.S.A.). Add to this mixture 10.00 grams of Surfonic AGM 550 (etheramine surfactant, available from Huntsman Corp., Houston, Tex., U.S.A.), and 0.10 g of sodium sulfite, 1.00 grams of propylene glycol. Mix until homogeneous.

c. Emulsion

Agitate the mono(isopropylammonium) N-(phosphonomethyl)glycine pre-mix under high shear (for example, in a Waring blender) and to it slowly add the carfentrazone-ethyl premix. Continue mixing for about five minutes. Continue mixing gently until homogeneous. The resulting mixture will be an emulsion formulation of mono (isopropylammonium) N-(phosphonomethyl)glycine and carfentrazone-ethyl. The final composition of the emulsion will be as follows:

| Ingredient | Weight Percent |
|---|---|
| carfentrazone-ethyl (95%) | 2.45 |
| Armul 1496/1505 HF | 5.00 |
| Aromatic 200 | 25.00 |
| mono(isopropylammonium) glyphosate (45.72% a.e.) | 36.05 (16.48 a.e.) |
| Surfonic AGM 550 | 10.00 |
| sodium sulfite | 0.10 |
| propylene glycol | 1.00 |
| Mazu 100DS silicone defoamer | 0.10 |

-continued

| Ingredient | Weight Percent |
|---|---|
| fumed silica | 2.00 |
| deionized water | 18.30 |

EXAMPLE 13

Carfentrazone-ethyl Emulsifiable Concentrate

To a 4:1 mixture of Aromatic 200/4-butyrolactone solvent is added 0.94 g of carfentrazone-ethyl, 5.00 g of Armul 1496 HF, and 5.00 g of Armul 1505 HF. The mixture is blended until homogeneous.

EXAMPLE 14

Biological Field Tests

N-(Phosphonomethyl)glycine and/or carfentrazone-ethyl spray compositions were prepared by mixing into water Roundup Ultra® herbicide (trade name for a herbicidal formulation containing approximately 360 g a.e./liter of mono(isopropylammonium) N-(phosphonomethyl)glycine, sold by Monsanto Company) and/or the carfentrazone-ethyl emulsifiable concentrate formulation prepared in Example 8. Plants were grown during the spring and summer in field plots measuring approximately 3.1 m by 7.5 m and through the duration of the test they received ambient light and were exposed to ambient temperatures. Test plots were located in Western, Midwestern, and Southern United States. Applications of the spray compositions were made using backpack sprayers calibrated to deliver a spray volume of approximately 93.4 liters per hectare (10 gallons per acre) using 11001, 110015, or 11002 FLATTAPR nozzles. The experimental design was a randomized complete block with three replications. Appropriate amounts of fertilizer were applied at the rate recommended for the production area. Percent inhibition ratings, which were a visual measurement of the effectiveness of each treatment in comparison to untreated plants, ranged from 0 to 100%. Inhibition of 0% indicates no effect, and inhibition of 100% indicates that all of the plants are completely dead.

For each plant species examined, treatments were made with N-(phosphonomethyl)glycine, with carfentrazone-ethyl, or with a composition containing a mixture of N-(phosphonomethyl)glycine and carfentrazone-ethyl at the rates indicated in Tables 3 through 8. Percent inhibition was measured at 3, 7 (or 8), and 21 days after treatment (DAT). Results for control of six plant species treated with various regimens of N-(phosphonomethyl)glycine and/or carfentrazone-ethyl, averaged for all sites of each treatment are shown in Tables 3 through 22.

TABLE 3

*Setaria faberi*
(Giant Foxtail)
(Average of 3 sites)

| | % Inhibition | | |
|---|---|---|---|
| Treatment | 3 DAT | 8 DAT | 21 DAT |
| 631 g a.e./ha glyphosate | 49 | 98 | 100 |
| 841 g a.e./ha glyphosate | 50 | 99 | 100 |
| 1262 g a.e./ha glyphosate | 58 | 100 | 100 |

TABLE 3-continued

*Setaria faberi*
(Giant Foxtail)
(Average of 3 sites)

| | % Inhibition | | |
|---|---|---|---|
| Treatment | 3 DAT | 8 DAT | 21 DAT |
| 35 g/ha carfentrazone-ethyl | 21 | 13 | 1 |
| 69.5 g/ha carfentrazone-ethyl | 36 | 27 | 2 |
| 35 g/ha carfentrazone-ethyl + 631 g a.e./ha glyphosate | 74 | 97 | 99 |
| 69.5 g/ha carfentrazone-ethyl + 631 g a.e./ha glyphosate | 79 | 97 | 100 |
| 35 g/ha carfentrazone-ethyl + 841 g a.e./ha glyphosate | 70 | 97 | 98 |
| 69.5 g/ha carfentrazone-ethyl + 841 g a.e./ha glyphosate | 78 | 98 | 100 |
| 35 g/ha carfentrazone-ethyl + 1262 g a.e./ha glyphosate | 76 | 100 | 100 |
| 69.5 g/hacarfentrazone-ethyl + 1262 g a.e./ha glyphosate | 78 | 99 | 100 |

TABLE 4

*Chenopodium album*
(Common Lambsquarter)
(Average of 3 sites)

| | % Inhibition | | |
|---|---|---|---|
| Treatment | 3 DAT | 8 DAT | 21 DAT |
| 631 g a.e./ha glyphosate | 62 | 93 | 99 |
| 69.5 g/ha carfentrazone-ethyl + 631 g a.e./ha glyphosate | 79 | 93 | 97 |
| 35 g/ha carfentrazone-ethyl + 841 g a.e./ha glyphosate | 78 | 93 | 99 |
| 69.5 g/ha carfentrazone-ethyl + 841 g a.e./ha glyphosate | 82 | 95 | 99 |
| 35 g/ha carfentrazone-ethyl + 1262 g a.e./ha glyphosate | 83 | 95 | 100 |
| 69.5 g/ha carfentrazone-ethyl + 1262 g a.e./ha glyphosate | 80 | 94 | 100 |

TABLE 5

*Abutilon theophrasti* (Velvetleaf) (Average of 3 sites)

| | % Inhibition | | |
|---|---|---|---|
| Treatment | 3 DAT | 8 DAT | 21 DAT |
| 631 g a.e./ha glyphosate | 62 | 93 | 99 |
| 841 g a.e./ha glyphosate | 33 | 67 | 87 |
| 1262 g a.e./ha glyphosate | 35 | 77 | 93 |
| 35 g/ha carfentrazone-ethyl | 52 | 47 | 27 |
| 69.5 g/ha carfentrazone-ethyl | 70 | 55 | 33 |
| 35 g/ha carfentrazone-ethyl + 631 g a.e./haglyphosate | 69 | 73 | 69 |
| 69.5 g/ha carfentrazone-ethyl + 631 g a.e./ha glyphosate | 70 | 79 | 79 |
| 35 g/ha carfentrazone-ethyl + 841 g a.e./ha glyphosate | 63 | 77 | 83 |
| 69.5 g/ha carfentrazone-ethyl + 841 ga.e./ha glyphosate | 69 | 78 | 88 |
| 35 g/ha carfentrazone-ethyl + 1262 g a.e./ha glyphosate | 66 | 86 | 91 |
| 69.5 g/ha carfentrazone-ethyl + 1262 g a.e./ha glyphosate | 71 | 84 | 89 |

TABLE 6

*Triticum spp.*
(Volunteer Wheat)
(Average of 2 sites)

| Treatment | % Inhibition | | |
|---|---|---|---|
| | 3 DAT | 8 DAT | 21 DAT |
| 631 g a.e./ha glyphosate | 13 | 39 | 82 |
| 841 g a.e./ha glyphosate | 14 | 53 | 97 |
| 1262 g a.e./ha glyphosate | 22 | 42 | 98 |
| 35 g/ha carfentrazone-ethyl | 12 | 13 | 4 |
| 69.5 g/ha carfentrazone-ethyl | 10 | 13 | 5 |
| 35 g/ha carfentrazone-ethyl + 631 g a.e./ha glyphosate | 23 | 48 | 83 |
| 69.5 g/ha carfentrazone-ethyl + 631 g a.e./ha glyphosate | 26 | 56 | 90 |
| 35 g/ha carfentrazone-ethyl + 841 g a.e./ha glyphosate | 25 | 59 | 97 |
| 69.5 g/ha carfentrazone-ethyl + 841 g a.e./ha glyphosate | 24 | 53 | 94 |
| 35 g/ha carfentrazone-ethyl + 1262 g a.e./ha glyphosate | 24 | 63 | 99 |
| 69.5 g4ha carfentrazone-ethyl + 1262 g a.e./ha glyphosate | 25 | 67 | 100 |

TABLE 7

*Ipomoea spp.*
(Morningglory)
(Average of 2 sites)

| Treatment | % Inhibition | | |
|---|---|---|---|
| | 3 DAT | 8 DAT | 21 DAT |
| 631 g a.e./ha glyphosate | 28 | 56 | 61 |
| 841 g a.e./ha glyphosate | 31 | 56 | 66 |
| 1262 g a.e./ha glyphosate | 36 | 67 | 72 |
| 35 g/ha carfentrazone-ethyl | 73 | 75 | 43 |
| 69.5 g/ha carfentrazone-ethyl | 80 | 85 | 61 |
| 35 g/ha carfentrazone-ethyl + 631 g a.e./ha glyphosate | 77 | 76 | 71 |
| 69.5 g/ha carfentrazone-ethyl + 631 g a.e./ha glyphosate | 85 | 91 | 90 |
| 35 g/ha carfentrazone-ethyl + 841 g a.e./ha glyphosate | 88 | 80 | 79 |
| 69.5 g/ha carfentrazone-ethyl + 841 g a.e./ha glyphosate | 84 | 90 | 90 |
| 35 g/ha carfentrazone-ethyl + 1262 g a.e./ha glyphosate | 79 | 84 | 87 |
| 69.5 g/ha carfentrazone-ethyl + 1262 g a.e./ha glyphosate | 83 | 94 | 93 |

TABLE 8

*Kochia sciparia*
(Kochia)
(Average of 2 sites)

| Treatment | % Inhibition | | |
|---|---|---|---|
| | 3 DAT | 8 DAT | 21 DAT |
| 631 g a.e./ha glyphosate | 27 | 50 | 77 |
| 841 g a.e./ha glyphosate | 24 | 58 | 90 |
| 1262 g a.e./ha glyphosate | 29 | 62 | 98 |
| 35 g/ha carfentrazone-ethyl | 18 | 23 | 56 |
| 69.5 g/ha carfentrazone-ethyl | 20 | 26 | 60 |
| 35 g/ha carfentrazone-ethyl + 631 g a.e./ha glyphosate | 29 | 57 | 92 |
| 69.5 g/ha carfentrazone-ethyl + 631 g a.e./ha glyphosate | 32 | 61 | 95 |
| 35 g/ha carfentrazone-ethyl + 841 g a.e./ha glyphosate | 33 | 59 | 100 |
| 69.5 g/ha carfentrazone-ethyl + 841 g a.e./ha glyphosate | 39 | 67 | 100 |
| 35 g/ha carfentrazone-ethyl + 1262 g a.e./ha glyphosate | 37 | 66 | 100 |
| 69.5 g/ha carfentrazone-ethyl + 1262 g a.e./ha glyphosate | 40 | 68 | 100 |

TABLE 9

*Bromus tectorum*
(Downy Brome)
(1 site)

| Treatment | % Inhibition | | |
|---|---|---|---|
| | 3 DAT | 8 DAT | 21 DAT |
| 631 g a.e./ha glyphosate | 40 | 82 | 100 |
| 841 g a.e./ha glyphosate | 37 | 88 | 99 |
| 1262 g a.e./ha glyphosate | 43 | 91 | 100 |
| 35 g/ha carfentrazone-ethyl | 20 | 30 | 21 |
| 69.5 g/ha carfentrazone-ethyl | 20 | 32 | 17 |
| 35 g/ha carfentrazone-ethyl + 631 g a.e./ha glyphosate | 48 | 84 | 98 |
| 69.5 g/ha carfentrazone-ethyl + 631 g a.e./ha glyphosate | 42 | 89 | 100 |
| 35 g/ha carfentrazone-ethyl + 841 g a.e./ha glyphosate | 47 | 92 | 100 |
| 69.5 g/ha carfentrazone-ethyl + 841 g a.e./ha glyphosate | 47 | 90 | 100 |
| 35 g/ha carfentrazone-ethyl + 1262 g a.e./ha glyphosate | 54 | 95 | 100 |
| 69.5 g/ha carfentrazone-ethyl + 1262 g a.e./ha glyphosate | 46 | 92 | 100 |

TABLE 10

*Lolium multiflorum*
(Italian Ryegrass)
(1 site)

| Treatment | % Inhibition | | |
|---|---|---|---|
| | 3 DAT | 8 DAT | 21 DAT |
| 631 g a.e./ha glyphosate | 42 | 87 | 94 |
| 841 g a.e./ha glyphosate | 41 | 85 | 94 |
| 1262 g a.e./ha glyphosate | 40 | 94 | 100 |
| 35 g/ha carfentrazone-ethyl | 12 | 15 | 0 |
| 69.5 g/ha carfentrazone-ethyl | 12 | 15 | 0 |
| 35 g/ha carfentrazone-ethyl + 631 g a.e./ha glyphosate | 38 | 76 | 89 |
| 69.5 g/ha carfentrazone-ethyl + 631 g a.e./ha glyphosate | 39 | 85 | 92 |
| 35 g/ha carfentrazone-ethyl + 841 g a.e./ha glyphosate | 40 | 82 | 91 |
| 69.5 g/ha carfentrazone-ethyl + 841 g a.e./ha glyphosate | 46 | 90 | 100 |
| 35 g/ha carfentrazone-ethyl + 1262 g a.e./ha glyphosate | 45 | 92 | 100 |
| 69.5 g/ha carfentrazone-ethyl + 1262 g a.e./ha glyphosate | 45 | 97 | 100 |

TABLE 11

*Brassica kaber*
(Wild Mustard)
(1 site)

| Treatment | % Inhibition | | |
|---|---|---|---|
| | 3 DAT | 8 DAT | 21 DAT |
| 631 g a.e./ha glyphosate | 20 | 79 | 96 |
| 841 g a.e./ha glyphosate | 26 | 83 | 100 |
| 1262 g a.e./ha glyphosate | 37 | 87 | 100 |
| 35 g/ha carfentrazone-ethyl | 27 | 23 | 0 |
| 69.5 g/ha carfentrazone-ethyl | 35 | 18 | 0 |
| 35 g/ha carfentrazone-ethyl + 631 g a.e./ha glyphosate | 33 | 79 | 96 |
| 69.5 g/ha carfentrazone-ethyl + 631 g a.e./ha glyphosate | 35 | 85 | 99 |
| 35 g/ha carfentrazone-ethyl + 841 g a.e./ha glyphosate | 29 | 84 | 99 |
| 69.5 g/ha carfentrazone-ethyl + 841 g a.e./ha glyphosate | 34 | 86 | 100 |
| 35 g/ha carfentrazone-ethyl + 1262 g a.e./ha glyphosate | 32 | 89 | 1OD |
| 69.5 g/ha carfentrazone-ethyl + 1262 g a.e./ha glyphosate | 35 | 89 | 99 |

TABLE 12

*Amaranthus retroflexus*
(Redroot Pigweed)
(1 site)

| Treatment | % Inhibition | | |
|---|---|---|---|
| | 3 DAT | 8 DAT | 21 DAT |
| 631 g a.e./ha glyphosate | 77 | 95 | 99 |
| 841 g a.e./ha glyphosate | 88 | 100 | 100 |
| 1262 g a.e./ha glyphosate | 88 | 99 | 99 |
| 35 g/ha carfentrazone-ethyl | 75 | 82 | 67 |
| 69.5 g/ha carfentrazone-ethyl | 67 | 85 | 93 |
| 35g/ha carfentrazone-ethyl + 631 g a.e./ha glyphosate | 87 | 95 | 97 |
| 69.5 g/ha carfentrazone-ethyl + 631 g a.e./ha glyphosate | 95 | 97 | 99 |
| 35 g/ha carfentrazone-ethyl + 841 g a.e./ha glyphosate | 92 | 91 | 96 |
| 69.5 g/ha carfentrazone-ethyl + 841 g a.e./ha glyphosate | 93 | 99 | 100 |
| 35 g/ha carfentrazone-ethyl + 1262 g a.e./ha glyphosate | 98 | 99 | 100 |
| 69.5 g/ha carfentrazone-ethyl + 1262 g a.e./ha glyphosate | 97 | 96 | 100 |

TABLE 13

*Amaranthus rudis*
(Common Waterhemp)
(1 site)

| Treatment | % Inhibition | | |
|---|---|---|---|
| | 3 DAT | 8 DAT | 21 DAT |
| 631 g a.e./ha glyphosate | 83 | 100 | 100 |
| 841 g a.e/ha glyphosate | 54 | 98 | 100 |
| 1262 g a.e./ha glyphosate | 38 | 100 | 100 |
| 35 g/ha carfentrazone-ethyl | 56 | 40 | 13 |
| 69.5 g/ha carfentrazone-ethyl | 86 | 56 | 10 |
| 35 g/ha carfentrazone-ethyl + 631 g a.e./ha glyphosate | 84 | 81 | 95 |
| 69.5 g/ha carfentrazone-ethyl + 631 g a.e./ha glyphosate | 78 | 100 | 100 |
| 35 g/ha carfentrazone-ethyl + 841 g a.e./ha glyphosate | 81 | 82 | 89 |
| 69.5 g/ha carfentrazone-ethyl + 841 g a.e./ha glyphosate | 89 | 92 | 90 |
| 35 g/ha carfentrazone-ethyl + 1262 g a.e./ha glyphosate | 86 | N.C. | 100 |
| 69.5 g/ha carfentrazone-ethyl + 1262 g a.e./ha glyphosate | 86 | 92 | 90 |

N.C. = Data not collected.

TABLE 14

*Brachiaria platyphylla*
(Broadleaf Signalgrass)
(1 site)

| Treatment | 3 DAT | 8 DAT | 21 DAT |
|---|---|---|---|
| 631 g a.e./ha glyphosate | 42 | 79 | 76 |
| 841 g a.e./ha glyphosate | 50 | 88 | 79 |
| 1262 g a.e./ha glyphosate | 48 | 92 | 86 |
| 35 g/ha carfentrazone-ethyl | 38 | 33 | 0 |
| 69.5 g/ha carfentrazone-ethyl | 43 | 38 | 13 |
| 35 g/ha carfentrazone-ethyl + 631 g a.e./ha glyphosate | 52 | 82 | 95 |
| 69.5 g/ha carfentrazone-ethyl + 631 g a.e./ha glyphosate | 57 | 83 | 100 |
| 35 g/ha carfentrazone-ethyl + 841 g a.e./ha glyphosate | 58 | 87 | 100 |
| 69.5 g/ha carfentrazone-ethyl + 841 g a.e./ha glyphosate | 62 | 85 | 100 |
| 35 g/ha carfentrazone-ethyl + 1262 g a.e./ha glyphosate | 57 | 92 | 98 |
| 69.5 g/ha carfentrazone-ethyl + 1262 g a.e./ha glyphosate | 65 | 92 | 100 |

TABLE 15

*Cassia obtusifolia*
(Sicklepod)
(1 site)

| Treatment | % Inhibition | | |
|---|---|---|---|
| | 3 DAT | 8 DAT | 21 DAT |
| 631 g a.e./ha glyphosate | 74 | 96 | 98 |
| 841 g a.e./ha glyphosate | 75 | 97 | 98 |
| 1262 g a.e./ha glyphosate | 80 | 99 | 97 |
| 35 g/ha carfentrazone-ethyl | 58 | 48 | 28 |
| 69.5 g/ha carfentrazone-ethyl | 60 | 60 | 38 |
| 35 g/ha carfentrazone-ethyl + 631 g a.e./ha glyphosate | 81 | 94 | 98 |
| 69.5 g/ha carfentrazone-ethyl + 631 g a.e./ha glyphosate | 89 | 97 | 97 |
| 35 g/ha carfentrazone-ethyl + 841 g a.e./ha glyphosate | 88 | 98 | 97 |
| 69.5 g/ha carfentrazone-ethyl + 841 g a.e./ha glyphosate | 81 | 92 | 98 |
| 35 g/ha carfentrazone-ethyl + 1262 g a.e./ha glyphosate | 82 | 98 | 99 |
| 69.5 g/ha carfentrazone-ethyl + 1262 g a.e./ha glyphosate | 82 | 99 | 99 |

TABLE 16

*Lolium perenne*
(Perennial Ryegrass)
(1 site)

| Treatment | % Inhibition | | |
|---|---|---|---|
| | 3 DAT | 8 DAT | 21 DAT |
| 631 g a.e./ha glyphosate | 20 | 63 | 92 |
| 841 g a.e./ha glyphosate | 19 | 69 | 96 |
| 1262 g a.e./ha glyphosate | 25 | 76 | 98 |
| 35 g/ha carfentrazone-ethyl | 8 | 18 | 14 |
| 69.5 g/ha carfentrazone-ethyl | 8 | 16 | 13 |
| 35 g/ha carfentrazone-ethyl + 631 g a.e./ha glyphosate | 23 | 64 | 91 |
| 69.5 g/ha carfentrazone-ethyl + 631 g a.e./ha glyphosate | 20 | 69 | 93 |
| 35 g/ha carfentrazone-ethyl + 841 g a.e./ha glyphosate | 26 | 68 | 95 |
| 69.5 g/ha carfentrazone-ethyl + 841 g a.e./ha glyphosate | 30 | 71 | 94 |
| 35 g/ha carfentrazone-ethyl + 1262 g a.e./ha glyphosate | 26 | 79 | 100 |
| 69.5 g/ha carfentrazone-ethyl + 1262 g a.e./ha glyphosate | 28 | 83 | 100 |

TABLE 17

*Malva Neglecta*
(Common Mallow)
(1 site)

| Treatment | % Inhibition | | |
|---|---|---|---|
| | 3 DAT | 8 DAT | 21 DAT |
| 631 g a.e./ha glyphosate | 43 | 62 | 77 |
| 841 g a.e./ha glyphosate | 43 | 63 | 83 |
| 1262 g a.e./ha glyphosate | 48 | 65 | 84 |
| 35 g/ha carfentrazone-ethyl | 67 | 65 | 74 |
| 69.5 g/ha carfentrazone-ethyl | 72 | 68 | 86 |
| 35 g/ha carfentrazone-ethyl + 631 g a.e./ha glyphosate | 72 | 80 | 93 |
| 69.5 g/ha carfentrazone-ethyl + 631 g a.e./ha glyphosate | 70 | 79 | 97 |
| 35 g/ha carfentrazone-ethyl + 841 g a.e./ha glyphosate | 73 | 80 | 100 |
| 69.5 g/ha carfentrazone-ethyl + 841 g a.e./ha glyphosate | 68 | 82 | 99 |
| 35 g/ha carfentrazone-ethyl + 1262 g a.e./ha glyphosate | 72 | 88 | 98 |
| 69.5 g/ha carfentrazone-ethyl + 1262 g a.e./ha glyphosate | 70 | 88 | 99 |

TABLE 18

*Polygonum convolvulus*
(Wild Buckwheat)
(1 site)

| Treatment | % Inhibition | | |
|---|---|---|---|
| | 3 DAT | 8 DAT | 21 DAT |
| 631 g a.e./ha glyphosate | 8 | 22 | 25 |
| 841 g a.e./ha glyphosate | 15 | 32 | 39 |
| 1262 g a.e./ha glyphosate | 38 | 46 | 63 |
| 35 g/ha carfentrazone-ethyl | 26 | 25 | 0 |
| 69.5 g/ha carfentrazone-ethyl | 28 | 23 | 0 |
| 35 g/ha carfentrazone-ethyl + 631 g a.e./ha glyphosate | 36 | 52 | 53 |
| 69.5 g/ha carfentrazone-ethyl + 631 g a.e./ha glyphosate | 34 | 55 | 49 |
| 35 g/ha carfentrazone-ethyl + 841 g a.e./ha glyphosate | 35 | 60 | 41 |
| 69.5 g/ha carfentrazone-ethyl + 841 g a.e./ha glyphosate | 40 | 64 | 53 |
| 35 g/ha carfentrazone-ethyl + 1262 g a.e./ha glyphosate | 47 | 65 | 69 |
| 69.5 g/ha carfentrazone-ethyl + 1262 g a.e./ha glyphosate | 51 | 73 | 61 |

TABLE 19

*Salsola iberica*
(Russian Thistle)
(1 site)

| Treatment | % Inhibition | | |
|---|---|---|---|
| | 3 DAT | 8 DAT | 21 DAT |
| 631 g a.e./ha glyphosate | 47 | 81 | 96 |
| 841 g a.e./ha glyphosate | 54 | 94 | 97 |
| 1262 g a.e./ha glyphosate | 52 | 99 | 100 |
| 35 g/ha carfentrazone-ethyl | 33 | 10 | 0 |
| 69.5 g/ha carfentrazone-ethyl | 25 | 12 | 0 |
| 35 g/ha carfentrazone-ethyl + 631 g a.e./ha glyphosate | 54 | 80 | 95 |
| 69.5 g/ha carfentrazone-ethyl + 631 g a.e./ha glyphosate | 65 | 93 | 98 |
| 35 g/ha carfentrazone-ethyl + 841 g a.e./ha glyphosate | 57 | 93 | 96 |
| 69.5 g/ha carfentrazone-ethyl + 841 g a.e./ha glyphosate | 61 | 94 | 99 |
| 35 g/ha carfentrazone-ethyl + 1262 g a.e./ha glyphosate | 67 | 97 | 100 |
| 69.5 g/ha carfentrazone-ethyl + 1262 g a.e./ha glyphosate | 61 | 95 | 96 |

TABLE 20

*Sesbania exaltata*
(Hemp Sesbania)
(1 site)

| Treatment | % Inhibition | | |
|---|---|---|---|
| | 3 DAT | 8 DAT | 21 DAT |
| 631 g a.e./ha glyphosate | 73 | 94 | 96 |
| 841 g a.e./ha glyphosate | 75 | 9.5 | 94 |
| 1262 g a.e./ha glyphosate | 75 | 99 | 93 |
| 35 g/ha carfentrazone-ethyl | 52 | 50 | 53 |
| 69.5 g/ha carfentrazone-ethyl | 65 | 60 | 60 |
| 35 g/ha carfentrazone-ethyl + 631 g a.e./ha glyphosate | 84 | 92 | 97 |
| 69.5 g/ha carfentrazone-ethyl + 63l g a.e./ha glyphosate | 85 | 99 | 100 |
| 35 g/ha carfentrazone-ethyl + 841 g a.e./ha glyphosate | 85 | 97 | 95 |
| 69.5 g/ha carfentrazone-ethyl + 841 g a.e./ha glyphosate | 86 | 97 | 100 |
| 35 g/ha carfentrazone-ethyl + 1262 g a.e./ha glyphosate | 78 | 97 | 98 |
| 69.5 g/ha carfentrazone-ethyl + 1262 g a.e./ha glyphosate | 81 | 99 | 100 |

TABLE 21

Sida spinosa
(Prickly Sida)
(1 site)

| Treatment | % Inhibition | | |
|---|---|---|---|
| | 3 DAT | 8 DAT | 21 DAT |
| 631 g a.e./ha glyphosate | 31 | 66 | 83 |
| 841 g a.e./ha glyphosate | 33 | 69 | 90 |
| 1262 g a.e./ha glyphosate | 34 | 75 | 97 |
| 35 g/ha carfentrazone-ethyl | 39 | 32 | 13 |
| 69.5 g/ha carfentrazone-ethyl | 42 | 40 | 23 |
| 35 g/ha carfentrazone-ethyl + 631 g a.e./ha glyphosate | 45 | 63 | 81 |
| 69.5 g/ha carfentrazone-ethyl + 631 g a.e./ha glyphosate | 44 | 74 | 85 |
| 35 g/ha carfentrazone-ethyl + 841 g a.e./ha glyphosate | 43 | 63 | 86 |
| 69.5 g/ha carfentrazone-ethyl + 841 g a.e./ha glyphosate | 49 | 65 | 87 |
| 35 g/ha carfentrazone-ethyl + 1262 g a.e./ha glyphosate | 45 | 77 | 94 |
| 69.5 g/ha carfentrazone-ethyl + 1262 g a.e./ha glyphosate | 47 | 81 | 96 |

TABLE 22

Sorghum halepense
(Johnsongrass)
(1 site)

| Treatment | % Inhibition | | |
|---|---|---|---|
| | 3 DAT | 8 DAT | 21 DAT |
| 631 g a.e./ha glyphosate | 58 | 91 | 97 |
| 841 g a.e./ha glyphosate | 60 | 94 | 98 |
| 1262 g a.e./ha glyphosate | 62 | 95 | 99 |
| 35 g/ha carfentrazone-ethyl | 39 | 27 | 9 |
| 69.5 g/ha carfentrazone-ethyl | 44 | 35 | 23 |
| 35 g/ha carfentrazone-ethyl + 631 g a.e./ha glyphosate | 65 | 88 | 97 |
| 69.5 g/ha carfentrazone-ethyl + 631 g a.e./ha glyphosate | 70 | 88 | 98 |
| 35 g/ha carfentrazone-ethyl + 841 g a.e./ha glyphosate | 70 | 92 | 99 |
| 69.5 g/ha carfentrazone-ethyl + 841 g a.e./ha glyphosate | 73 | 94 | 99 |
| 35 g/ha carfentrazone-ethyl + 1262 g a.e./ha glyphosate | 70 | 94 | 99 |
| 69.5 g/ha carfentrazone-ethyl + 1262 g a.e./ha glyphosate | 73 | 96 | 100 |

The examples herein can be performed by substituting the generically or specifically described ingredients and/or operating conditions of this invention for those used in the preceding examples.

The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A combination comprising:
   (a) N-(phosphonomethyl)glycine, or a salt thereof; and
   (b) a triazolinone herbicide having the structure of formula (II):

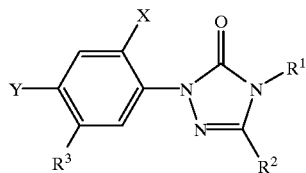

or a salt of (II) or a tautomer of (II), wherein:
   $R^1$ is haloalkyl;
   $R^2$ is selected from the group consisting of halogen and lower alkyl;
   $R^3$ is —$NHSO_2R^5$;
   $R^5$ is selected from the group consisting of alkyl, haloalkyl, dialkylamino, carboxyalkyl, hydroxy, and aryl;
   X is selected from the group consisting of H, halo, alkyl, alkoxy, haloalkyl, and nitro; and
   Y is selected from the group consisting of H, halogen, alkyl, alkoxy, haloalkyl, haloloweralkylsulfinyl, and haloloweralkoxy.

2. The combination of claim 1 wherein $R^5$ is alkyl.

3. The combination of claim 2 wherein $R^5$ is from $C_1$ to about $C_5$ alkyl.

4. The combination of claim 3 wherein $R^5$ is ethyl.

5. The combination of claim 4 wherein the triazolinone herbicide comprises sulfentrazone.

6. The combination of claim 1 wherein the N-(phosphonomethyl)glycine is present in a water soluble salt form.

7. The combination of claim 6 wherein the salt of N-(phosphonomethyl)glycine comprises mono (isopropylammonium) N-(phosphonomethyl)glycine.

8. The combination of claim 6 wherein the salt of N-(phosphonomethyl)glycine comprises mono (trimethylsulfonium) N-(phosphonomethyl)glycine.

9. The combination of claim 6 wherein the salt of N-(phosphonomethyl)glycine comprises monoammonium N-(phosphonomethyl)glycine.

10. The combination of claim 6 wherein the salt of N-(phosphonomethyl)glycine comprises mono(2-hydroxyethylammonium) N-(phosphonomethyl)glycine.

11. The combination of claim 1 wherein the weight ratio of N-(phosphonomethyl)glycine acid equivalents to the triazolinone herbicide is about 1:1 to about 100:1.

12. The combination of claim 11 wherein the weight ratio of N-(phosphonomethyl)glycine acid equivalents to the triazolinone herbicide is about 2:1 to about 75:1.

13. The combination of claim 12 wherein the weight ratio of N-(phosphonomethyl)glycine acid equivalents to the triazolinone herbicide is about 5:1 to about 50:1.

14. The combination of claim 13 wherein the weight ratio of N-(phosphonomethyl)glycine acid equivalents to the triazolinone herbicide is about 10:1 to about 40:1.

15. The combination of claim 1 further comprising a surfactant.

16. The combination of claim 15 wherein the surfactant comprises a compound selected from the group consisting of an ethoxylated alkyl amine, an ethoxylated alkyl polyamine, an alkylpolyglucoside, an alkoxylated acetylenic diol, a polyoxyalkylene alkyl ether, an organosilicone, an ethoxylated alcohol, an ethoxylated Guerbet alcohol, an alkylphenol ethoxylate, a sulfated polyoxyalkylene alkylphenol, an alcohol sulfate, a polyoxyalkylene alcohol sulfate, a monoalcoholphosphate, a dialcoholphosphate, a mono (polyoxyalkylene alcohol)phosphate, a di(polyoxyalkylene alcohol)phosphate, a mono(polyoxyalkylene alkylphenol) phosphate, a di(polyoxyalkylene alkylphenol)phosphate, a polyoxyalkylene alkylphenol carboxylate, a polyoxyalkylene alcohol carboxylate, a fluorinated compound, an etheramine, an alkylsulfonate, an alkylphenylsulfonate, an alkylsulfate, an alkylphenolsulfate, an alkyl betaine, an alkyl carboxylate (including fatty acids, fatty acid salts, and pelargonic acid), an ethoxylated alkylamide, a quaternary alkylamine, and combinations thereof.

17. The combination of claim 16 wherein the surfactant comprises a compound selected from the group consisting of an ethoxylated alkyl amine, an alkylpolyglucoside, an etheramine, a quaternary alkylamine, and combinations thereof.

18. The combination of claim 17 wherein the surfactant comprises an ethoxylated alkylamine.

19. The combination of claim 17 wherein the surfactant is an etheramine surfactant.

20. The combination of claim 19 wherein the etheramine surfactant has the chemical structure:

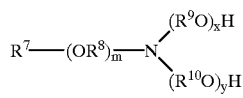

wherein $R^7$ is a moiety selected from the group consisting of about $C_6$ to about $C_{22}$ alkyl, aryl, and alkylaryl; m is an average number from 1 to about 10; $R^8$ is $C_1$ to about $C_4$ alkylene; $R^9$ and $R^{10}$ are independently $C_1$ to about $C_4$ alkylene groups; and x and y are average numbers such that the sum of x and y is in the range from 2 to about 60.

21. A composition comprising:
  (a) N-(phosphonomethyl)glycine or a salt thereof;
  (b) a triazolinone herbicide;
  (c) an alkoxylated acetylenic diol surfactant; and
  (d) a polyoxyalkylene alkyl ether surfactant;
wherein the triazolinone herbicide has the structure of formula (II):

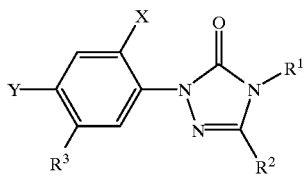

or a tautomer thereof, wherein:
  $R^1$ is haloalkyl;
  $R^2$ is selected from the group consisting of halogen and lower alkyl;
  $R^3$ is selected from the group consisting of $-CH_2CHClCO_2R^4$ and $-NHSO_2R^5$;
  $R^4$ is selected from the group consisting of alkyl, alkoxycarbonylalkyl, cycloalkyl, benzyl, chlorobenzyl, alkylbenzyl, and haloalkylbenzyl;
  $R^5$ is selected from the group consisting of alkyl, haloalkyl, dialkylamino, carboxymethyl, hydroxy, and aryl;
  X is selected from the group consisting of hydrogen, halogen, alkyl, alkoxy, haloalkyl, and nitro; and
  Y is selected from the group consisting of hydrogen, halogen, alkyl, alkoxy, haloalkyl, halo lower alkylsulfinyl, and halo lower alkoxy.

22. The composition of claim 21 wherein the weight ratio of N-(phosphonomethyl)glycine or salt thereof expressed as an acid equivalent to the triazolinone herbicide is in the range of about 1:1 to about 100:1.

23. The composition of claim 22 wherein the weight ratio of N-(phosphonomethyl)glycine or salt thereof expressed as an acid equivalent to the triazolinone herbicide is in the range of about 2:1 to about 75:1.

24. The composition of claim 23 wherein the weight ratio of N-(phosphonomethyl)glycine or salt thereof expressed as an acid equivalent to the triazolinone herbicide is in the range of about 5:1 to about 50:1.

25. The composition of claim 24 wherein the weight ratio of N-(phosphonomethyl)glycine or salt thereof expressed as an acid equivalent to the triazolinone herbicide is in the range of about 10:1 to about 40:1.

26. The composition of claim 21 wherein $R^3$ of the triazolinone herbicide is $-CH_2CHClCO_2R^4$.

27. The composition of claim 26 wherein the triazolinone herbicide comprises carfentrazone-ethyl.

28. The composition of claim 21 wherein $R^3$ of the triazolinone herbicide is $-NHSO_2R^5$.

29. The composition of claim 28 wherein the triazolinone herbicide comprises sulfentrazone.

30. The composition of claim 21 further comprising a solvent.

31. The composition of claim 30 wherein the solvent is selected from the group consisting of a phosphate solvent, an aromatic solvent, a polyarylalkyl solvent, a polyoxylated trialkylphenylether solvent, an aliphatic solvent, dimethylformamide, 4-butyrolactone, and N-methylpyrrolidone.

32. The composition of claim 30 wherein the solvent comprises an aromatic solvent.

33. The composition of claim 32 wherein the solvent is selected from the group consisting of o-xylene, m-xylene, and p-xylene.

34. The composition of claim 30 wherein the solvent comprises a phosphate solvent.

35. The composition of claim 34 wherein the solvent comprises 2-ethylhexyl diphenyl phosphate.

36. The composition of claim 34 wherein the solvent comprises trixylenyl phosphate.

37. The composition of claim 30 wherein the solvent comprises phenylxylylethane.

38. The composition of claim 21 further comprising an alkoxylated organosilicone surfactant.

39. The composition of claim 21 further comprising a carrier.

40. The composition of claim 39 wherein the carrier is present in a concentration of up to about 85% by weight.

41. The composition of claim 40 wherein the carrier is present in a concentration of up to about 80% by weight.

42. The composition of claim 40 wherein the carrier is present in a concentration of up to about 70% by weight.

43. The composition of claim 39 wherein the carrier comprises ammonium sulfate.

44. The composition of claim 21 wherein the alkoxylated acetylenic diol surfactant is present in a concentration of from about 1% by weight to about 15% by weight.

45. The composition of claim 44 wherein the alkoxylated acetylenic diol surfactant is present in a concentration of from about 1% by weight to about 10% by weight.

46. The composition of claim 45 wherein the alkoxylated acetylenic diol surfactant is present in a concentration of from about 2% by weight to about 8% by weight.

47. The composition of claim 21 wherein the alkoxylated acetylenic diol surfactant comprises about 1 mole to about 50 moles of ethylene oxide per molecule of surfactant.

48. The composition of claim 47 wherein the alkoxylated acetylenic diol surfactant comprises about 3 moles to about 30 moles of ethylene oxide per molecule of surfactant.

49. The composition of claim 48 wherein the alkoxylated acetylenic dial surfactant comprises about 5 moles to about 20 moles of ethylene oxide per molecule of surfactant.

50. The composition of claim 21 wherein the alkoxylated acetylenic diol surfactant comprises an ethoxylated tetramethyldecynediol.

51. A composition comprising N-(phosphonomethyl)glycine or a salt thereof, and a triazolinone herbicide having the structure of formula (V):

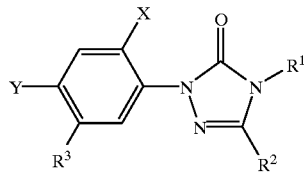

(V)

or a tautomer thereof, wherein:
$R^1$ is haloalkyl;
$R^2$ is selected from the group consisting of halogen and lower alkyl;
$R^3$ is selected from the group consisting of —CH$_2$CHClCO$_2$R$^6$ and —NHSO$_2$R$^5$;
$R^6$ is selected from the group consisting of H, alkyl, alkoxycarbonylalkyl, cycloalkyl, benzyl, chlorobenzyl, alkylbenzyl, and haloalkylbenzyl;
$R^5$ is selected from the group consisting of alkyl, haloalkyl, dialkylamino, carboxymethyl, hydroxy, and aryl;
X is selected from the group consisting of hydrogen, halogen, alkyl, alkoxy, haloalkyl, and nitro; and
Y is selected from the group consisting of hydrogen, halogen, alkyl, alkoxy, haloalkyl, halo lower alkylsulfinyl, and halo lower alkoxy;
and wherein the N-(phosphonomethyl)glycine or salt thereof is substantially dissolved in an aqueous phase and the triazolinone herbicide is substantially dissolved in a hydrophobic phase.

52. The composition of claim 51 wherein the weight ratio of N-(phosphonomethyl)glycine or salt thereof expressed as an acid equivalent to the triazolinone herbicide is in the range of about 1:1 to about 100:1.

53. The composition of claim 52 wherein the weight ratio of N-(phosphonomethyl)glycine or salt thereof expressed as an acid equivalent to the triazolinone herbicide is in the range of about 2:1 to about 75:1.

54. The composition of claim 53 wherein the weight ratio of N-(phosphonomethyl)glycine or salt thereof expressed as an acid equivalent to the triazolinone herbicide is in the range of about 5:1 to about 50:1.

55. The composition of claim 54 wherein the weight ratio of N-(phosphonomethyl)glycine or salt thereof expressed as an acid equivalent to the triazolinone herbicide is in the range of about 10:1 to about 40:1.

56. The composition of claim 51 wherein the hydrophobic phase is dispersed in the aqueous phase, thereby forming an emulsion.

57. The composition of claim 56 wherein the hydrophobic phase further comprises an emulsifier.

58. The composition of claim 57 wherein the emulsifier comprises an anionic surfactant.

59. The composition of claim 58 wherein the emulsifier comprises an alkylbenzenesulfonic acid salt.

60. The composition of claim 59 wherein the emulsifier comprises calcium dodecylbenzenesulfonate.

61. The composition of claim 54 wherein the emulsifier further comprises a nonionic surfactant.

62. The composition of claim 56 wherein the hydrophobic phase further comprises an emulsion stabilizer.

63. The composition of claim 62 wherein the emulsion stabilizer comprises silica.

64. The composition of claim 56 wherein the hydrophobic phase further comprises a defoamer.

65. The composition of claim 56 wherein the aqueous phase further comprises a surfactant.

66. The composition of claim 65 wherein the surfactant comprises a compound selected from the group consisting of an ethoxylated alkyl amine, an ethoxylated alkyl polyamine, an alkylpolyglucoside, an alkoxylated acetylenic diol, a polyoxyalkylene alkyl ether, an organosilicone, an ethoxylated alcohol, an ethoxylated Guerbet alcohol, an alkylphenol ethoxylate, a sulfated polyoxyalkylene alkylphenol, an alcohol sulfate, a polyoxyalkylene alcohol sulfate, a monoalcoholphosphate, a dialcoholphosphate, a mono(polyoxyalkylene alcohol)phosphate, a di(polyoxyalkylene alcohol)phosphate, a mono(polyoxyalkylene alkylphenol)phosphate, a di(polyoxyalkylene alkylphenol)phosphate, a polyoxyalkylene alkylphenol carboxylate, a polyoxyalkylene alcohol carboxylate, a fluorinated compound, an etheramine, an alkylsulfonate, an alkylphenylsulfonate, an alkylsulfate, an alkylphenolsulfate, an alkyl betaine, an alkyl carboxylate, an ethoxylated alkylamide, a quaternary alkylamine, and combinations thereof.

67. The composition of claim 66 wherein the surfactant comprises a compound selected from the group consisting of an ethoxylated alkyl amine, an alkylpolyglucoside, an etheramine, a quaternary alkylamine, and combinations thereof.

68. The composition of claim 67 wherein the surfactant comprises an ethoxylated alkylamine.

69. The composition of claim 66 wherein the surfactant comprises an etheramine.

70. The composition of claim 56 wherein the aqueous phase comprises a salt of N-(phosphonomethyl)glycine.

71. The composition of claim 70 wherein the aqueous phase comprises the monoisopropylammonium salt of N-(phosphonomethyl)glycine.

72. The composition of claim 70 wherein the aqueous phase comprises the mono(2-hydroxyethylammonium) salt of N-(phosphonomethyl)glycine.

73. The composition of claim 56 wherein:
the aqueous phase comprises the mono(isopropylammonium) salt of N-(phosphonomethyl)glycine), an ethoxylated alkylamine surfactant, sodium sulfite, propylene glycol, and water; and
the hydrophobic phase comprises carfentrazone-ethyl, an aromatic solvent, calcium dodecylbenzenesulfonate, a nonionic surfactant, and a silicone defoamer; and
wherein the hydrophobic phase is dispersed in the aqueous phase to form an emulsion.

74. A process for the preparation of a herbicidal composition wherein the method comprises:
(a) providing a hydrophobic solution comprising a triazolinone herbicide;
(b) providing an aqueous solution comprising N-(phosphonomethyl)glycine or a salt thereof; and (c) dispersing the hydrophobic solution into the aqueous solution to form an emulsion;

wherein the triazolinone herbicide having the structure of formula (V):

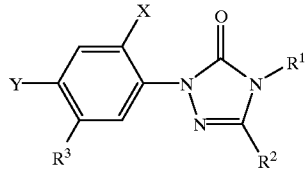

(V)

or a tautomer thereof, wherein:

$R^1$ is haloalkyl;

$R^2$ is selected from the group consisting of halogen and lower alkyl;

$R^3$ is selected from the group consisting of —$CH_2CHClCO_2R^6$ and —$NHSO_2R^5$;

$R^6$ is selected from the group consisting of H, alkyl, alkoxycarbonylalkyl, cycloalkyl, benzyl, chlorobenzyl, alkylbenzyl, and haloalkylbenzyl;

$R^5$ is selected from the group consisting of alkyl, haloalkyl, dialkylamino, carboxymethyl, hydroxy, and aryl;

X is selected from the group consisting of hydrogen, halogen, alkyl, alkoxy, haloalkyl, and nitro; and Y is selected from the group consisting of hydrogen, halogen, alkyl, alkoxy, haloalkyl, halo lower alkylsulfinyl, and halo lower alkoxy.

75. The process of claim 74 wherein the hydrophobic solution further comprises an emulsifier.

76. The composition of claim 75 wherein the emulsifier comprises an anionic surfactant.

77. The composition of claim 76 wherein the emulsifier comprises an alkylbenzenesulfonic acid salt.

78. The composition of claim 77 wherein the emulsifier comprises calcium dodecylbenzenesulfonate.

79. The composition of claim 76 wherein the emulsifier further comprises a nonionic surfactant.

80. The composition of claim 75 wherein the hydrophobic solution further comprises an emulsion stabilizer.

81. The composition of claim 80 wherein the emulsion stabilizer comprises silica.

82. The composition of claim 74 wherein the hydrophobic solution further comprises a defoamer.

83. The composition of claim 74 wherein the aqueous solution further comprises a surfactant.

84. A process for the preparation of a herbicidal composition wherein the method comprises:

(a) providing a mixture comprising:
(i) a triazolinone herbicide;
(ii) an alkoxylated acetylenic diol surfactant; and
(iii) a polyoxyalkylene alkyl ether surfactant; and (b) combining the mixture of step (a) with N-(phosphonomethyl)glycine or a salt thereof to form a dough;

wherein the triazolinone herbicide has the structure of formula (II):

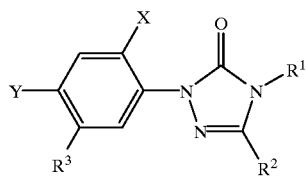

(II)

or a tautomer thereof, wherein:

$R^1$ is haloalkyl;

$R^2$ is selected from the group consisting of halogen and lower alkyl;

$R^3$ is selected from the group consisting of —$CH_2CHClCO_2R^4$ and —$NHSO_2R^5$;

$R^4$ is selected from the group consisting of alkyl, alkoxycarbonylalkyl, cycloalkyl, benzyl, chlorobenzyl, alkylbenzyl, and haloalkylbenzyl;

$R^5$ is selected from the group consisting of alkyl, haloalkyl, dialkylamino, carboxymethyl, hydroxy, and aryl;

X is selected from the group consisting of hydrogen, halogen, alkyl, alkoxy, haloalkyl, and nitro; and Y is selected from the group consisting of hydrogen, halogen, alkyl, alkoxy, haloalkyl, halo lower alkylsulfinyl, and halo lower alkoxy.

85. The process of claim 84 wherein $R^3$ of the triazolinone herbicide is —$CH_2CHClCO_2R^4$.

86. The process of claim 85 wherein the triazolinone herbicide comprises carfentrazone-ethyl.

87. The process of claim 84 wherein $R^3$ of the triazolinone herbicide is —$NHSO_2R^5$.

88. The process of claim 87 wherein the triazolinone herbicide comprises sulfentrazone.

89. The process of claim 84 wherein the mixture of step (a) further comprises a solvent.

90. The process of claim 89 wherein the solvent is selected from the group consisting of a phosphate solvent, an aromatic solvent, a polyarylalkyl solvent, a polyoxylated trialkylphenylether solvent, an aliphatic solvent, dimethylformamide, 4-butyrolactone, and N-methylpyrrolidone.

91. The process of claim 90 wherein the solvent comprises an aromatic solvent.

92. The process of claim 91 wherein the solvent is selected from the group consisting of o-xylene, m-xylene, and p-xylene.

93. The process of claim 90 wherein the solvent comprises a phosphate solvent.

94. The process of claim 93 wherein the solvent comprises 2-ethylhexyl diphenyl phosphate.

95. The process of claim 93 wherein the solvent comprises trixylenyl phosphate.

96. The process of claim 89 further comprising the step of shaping the dough.

97. The process of claim 96 wherein the shaping step comprises extruding the dough.

98. The process of claim 96 further comprising the step of drying the shaped dough.

99. The process of claim 84 wherein the mixture in which the triazolinone herbicide is dissolved further comprises an alkoxylated organosilicone surfactant.

100. The process of claim 99 wherein the mixture in which the triazolinone herbicide is dissolved further comprises a solvent selected from the group consisting of a phosphate solvent, an aromatic solvent, a polyarylalkyl solvent, a polyoxylated trialkylphenylether solvent, an aliphatic solvent, dimethylformamide, 4-butyrolactone, and N-methylpyrrolidone.

101. The process of claim 84 wherein step (b) further comprises adding a carrier.

102. The process of claim 101 wherein the carrier comprises ammonium sulfate.

103. A method of treating plants wherein the method comprises contacting foliage of a plant with a biologically effective amount of a combination comprising N-(phosphonomethyl)glycine or a salt thereof, and a triazolinone herbicide, wherein the triazolinone herbicide has the structure of formula (II):

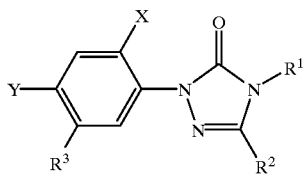

(II)

or a tautomer thereof, wherein:

$R^1$ is haloalkyl;

$R^2$ is selected from the group consisting of halogen and lower alkyl;

$R^3$ is —$NHSO_2R^5$;

$R^5$ is selected from the group consisting of alkyl, haloalkyl, dialkylamino, carboxymethyl, hydroxy, and aryl;

X is selected from the group consisting of hydrogen, halogen, alkyl, alkoxy, haloalkyl, and nitro; and Y is selected from the group consisting of hydrogen, halogen, alkyl, alkoxy, haloalkyl, haloloweralkylsulfinyl, and haloloweralkoxy.

104. The method of claim 103 wherein the triazolinone herbicide comprises sulfentrazone.

105. The method of claim 103 wherein the combination comprises a composition comprising:

(a) N-(phosphonomethyl)glycine or a salt thereof;

(b) a triazolinone herbicide;

(c) an alkoxylated acetylenic diol surfactant; and (d) a polyoxyalkylene alkyl ether surfactant.

106. The method of claim 103 wherein the combination comprises a composition wherein the N-(phosphonomethyl) glycine or salt thereof is substantially dissolved in an aqueous phase, the triazolinone herbicide is substantially dissolved in a hydrophobic phase, and the hydrophobic phase is dispersed in the aqueous phase to form an emulsion.

* * * * *